US009456985B2

(12) United States Patent
Wertz et al.

(10) Patent No.: US 9,456,985 B2
(45) Date of Patent: *Oct. 4, 2016

(54) SUSTAINED-RELEASED PRODUCT COMPRISING A COMBINATION OF A NON-OPIOID AMINE AND A NON-STEROIDAL, ANTI-INFLAMMATORY DRUG

(71) Applicant: Upsher-Smith Laboratories, Inc., Maple Grove, MN (US)

(72) Inventors: Christian F. Wertz, St. Louis Park, MN (US); James S. Jensen, Edina, MN (US); Victoria Ann O'Neill, Wayzata, MN (US); Sean B. Mahoney, Plymouth, MN (US); Stephen M. Berge, Shoreview, MN (US)

(73) Assignee: UPSHER-SMITH LABORATORIES, INC., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/697,891

(22) Filed: Apr. 28, 2015

(65) Prior Publication Data

US 2015/0238423 A1 Aug. 27, 2015

Related U.S. Application Data

(63) Continuation of application No. 13/496,818, filed as application No. PCT/US2009/069912 on Dec. 31, 2009, now Pat. No. 9,023,390.

(60) Provisional application No. 61/243,391, filed on Sep. 17, 2009.

(51) Int. Cl.
| | |
|---|---|
| *A61K 9/20* | (2006.01) |
| *A61K 31/44* | (2006.01) |
| *A61K 31/19* | (2006.01) |
| *A61K 31/13* | (2006.01) |
| *A61K 31/135* | (2006.01) |
| *A61K 31/46* | (2006.01) |
| *A61K 31/485* | (2006.01) |
| *A61K 31/138* | (2006.01) |
| *A61K 31/192* | (2006.01) |

(52) U.S. Cl.
CPC ............ *A61K 9/2054* (2013.01); *A61K 9/2013* (2013.01); *A61K 31/13* (2013.01); *A61K 31/135* (2013.01); *A61K 31/138* (2013.01); *A61K 31/19* (2013.01); *A61K 31/192* (2013.01); *A61K 31/46* (2013.01); *A61K 31/485* (2013.01)

(58) Field of Classification Search
None
See application file for complete search history.

(56) References Cited

U.S. PATENT DOCUMENTS

| | | | |
|---|---|---|---|
| 4,834,965 | A | 5/1989 | Martani et al. |
| 5,206,262 | A | 4/1993 | Donati et al. |
| 5,330,766 | A | 7/1994 | Morella et al. |
| 5,368,852 | A | 11/1994 | Umemoto et al. |
| 5,378,474 | A | 1/1995 | Morella et al. |
| 5,516,803 | A | 5/1996 | Raffa |
| 5,580,578 | A | 12/1996 | Oshlack et al. |
| 5,639,476 | A | 6/1997 | Oshlack et al. |
| 5,914,129 | A | 6/1999 | Mauskop |
| 5,958,452 | A | 9/1999 | Oshlack et al. |
| 5,958,459 | A | 9/1999 | Chasin et al. |
| 5,965,161 | A | 10/1999 | Oshlack et al. |
| 5,968,551 | A | 10/1999 | Oshlack et al. |
| 6,068,855 | A | 5/2000 | Leslie et al. |
| 6,127,352 | A | 10/2000 | Uribe |
| 6,143,353 | A | 11/2000 | Oshlack et al. |
| 6,261,599 | B1 | 7/2001 | Oshlack et al. |
| 6,294,195 | B1 | 9/2001 | Oshlack et al. |
| 6,335,033 | B2 | 1/2002 | Oshlack et al. |
| 6,695,088 | B2 | 2/2004 | Oshlack et al. |
| 6,696,066 | B2 | 2/2004 | Kaiko et al. |
| 6,699,502 | B1 | 3/2004 | Fanara et al. |
| 6,706,281 | B2 | 3/2004 | Oshlack et al. |
| 6,733,783 | B2 | 5/2004 | Oshlack et al. |
| 6,743,442 | B2 | 6/2004 | Oshlack et al. |
| 6,902,742 | B2 | 6/2005 | Devane et al. |
| 6,905,709 | B2 | 6/2005 | Oshlack et al. |
| 7,070,806 | B2 | 7/2006 | Oshlack et al. |
| 7,083,807 | B2 | 8/2006 | Fanara et al. |
| 7,172,767 | B2 | 2/2007 | Kaiko et al. |
| 7,192,966 | B2 | 3/2007 | Mayo-Alvarez et al. |
| 7,201,920 | B2 | 4/2007 | Kumar et al. |
| 7,794,750 | B2 | 9/2010 | Naringrekar et al. |
| 7,906,141 | B2 | 3/2011 | Ziegler et al. |

(Continued)

FOREIGN PATENT DOCUMENTS

| | | |
|---|---|---|
| AU | 781058 | 3/2001 |
| DE | 10023699 | 4/2001 |

(Continued)

OTHER PUBLICATIONS

"Future Opioids. The Birth of a New Generation" [retrieved on Jun. 15, 2011]. Retrieved from the internet: URL:http://www.opioids. coml 7 pages.
International Search Report and Written Opinion issued Jul. 9, 2010, by the European Patent Office. Patent Application No. PCT/US2009/069902.
"Aerosol.RTM. OT surfacants" datasheet, Cytec Industries, Inc., West Paterson, NJ, copyright 2000; 6 pgs.

(Continued)

*Primary Examiner* — Jessica Worsham
(74) *Attorney, Agent, or Firm* — Mueting, Raasch & Gebhardt, P.A.

(57) ABSTRACT

Sustained-release oral pharmaceutical compositions and methods of use, wherein the compositions are in a single dosage form and include an amine-containing compound (including salts thereof), a salt of a non-steroidal anti-inflammatory drug (NSAID), and a hydrophilic matrix.

19 Claims, 6 Drawing Sheets

(56) References Cited

U.S. PATENT DOCUMENTS

| | | |
|---|---|---|
| 9,023,390 B2 | 5/2015 | Wertz et al. |
| 2002/0058050 A1 | 5/2002 | Sackler et al. |
| 2002/0176888 A1 | 11/2002 | Bartholomaeus et al. |
| 2003/0035837 A1 | 2/2003 | Sackler et al. |
| 2003/0044464 A1 | 3/2003 | Ziegler et al. |
| 2003/0049317 A1 | 3/2003 | Lindsay |
| 2003/0049318 A1 | 3/2003 | Davis et al. |
| 2003/0065002 A1 | 4/2003 | Caruso et al. |
| 2003/0068375 A1 | 4/2003 | Wright et al. |
| 2003/0092724 A1 | 5/2003 | Kao et al. |
| 2004/0062812 A1 | 4/2004 | Maloney |
| 2004/0204413 A1 | 10/2004 | Faour et al. |
| 2004/0224020 A1 | 11/2004 | Schoenhard |
| 2004/0266807 A1 | 12/2004 | Oshlack et al. |
| 2005/0020613 A1 | 1/2005 | Boehm et al. |
| 2005/0074493 A1 | 4/2005 | Mehta et al. |
| 2005/0080012 A1 | 4/2005 | Mickle et al. |
| 2005/0123606 A1 | 6/2005 | Kidane |
| 2005/0158382 A1 | 7/2005 | Cruz et al. |
| 2005/0169990 A1 | 8/2005 | Kao et al. |
| 2005/0191343 A1 | 9/2005 | Liang |
| 2005/0245483 A1 | 11/2005 | Brogmann et al. |
| 2006/0003008 A1 | 1/2006 | Gibson et al. |
| 2006/0034872 A1 | 2/2006 | Woolf |
| 2006/0083690 A1 | 4/2006 | Chang |
| 2006/0110327 A1 | 5/2006 | Emigh et al. |
| 2006/0177380 A1 | 8/2006 | Emigh et al. |
| 2006/0210625 A1 | 9/2006 | Kidane |
| 2006/0251721 A1 | 11/2006 | Cruz et al. |
| 2006/0286174 A1 | 12/2006 | Raman et al. |
| 2007/0020339 A1 | 1/2007 | Bear |
| 2007/0142421 A1 | 6/2007 | Mayo-Alvarez et al. |
| 2007/0281016 A1 | 12/2007 | Kao et al. |
| 2007/0281018 A1 | 12/2007 | Qiu et al. |
| 2008/0008659 A1 | 1/2008 | Guimberteau et al. |
| 2008/0014228 A1 | 1/2008 | Darmuzey et al. |
| 2008/0031901 A1 | 2/2008 | Qiu et al. |
| 2009/0214648 A1 | 8/2009 | Kandakatla et al. |
| 2011/0275658 A1 | 11/2011 | Evenstad et al. |
| 2013/0237559 A1 | 9/2013 | Ortiz et al. |

FOREIGN PATENT DOCUMENTS

| | | |
|---|---|---|
| EP | 0009808 | 4/1980 |
| EP | 0546676 | 6/1993 |
| EP | 0649657 | 4/1995 |
| EP | 1293195 | 3/2003 |
| EP | 1384471 | 1/2004 |
| EP | 2074990 | 7/2009 |
| EP | 2085075 | 8/2009 |
| WO | WO 9852545 A1 | 11/1998 |
| WO | WO0004879 | 2/2000 |
| WO | WO0115667 | 3/2001 |
| WO | WO2007022356 | 2/2007 |
| WO | WO 2007/072503 A2 | 6/2007 |
| WO | WO2007022356 | 11/2007 |
| WO | WO2010078486 | 7/2010 |
| WO | WO2010078486 | 8/2010 |
| WO | WO 2011/034554 A1 | 3/2011 |
| WO | WO2012003231 | 1/2012 |

OTHER PUBLICATIONS

"Future Opioids. The Birth of a New Generation," [retrieved on Jun. 15, 2011]. Retrieved from the internet: <URL:http://www.opioids.com>; 7 pgs.

Ahmed et al, "In vitro release kinetics study of naproxen from swellable hydrophilic matrix tablets" 2010. Bangladesh Phar Journal. 13:18-22.

Baveja et al. "Influence of surfactants on drug release from hydroxypropylmethylcellulose matrices." 1988. Int. J. Pharmaceutics. 41:83-90.

Bhatt et al., "Saccharin as a salt former. Enhanced solubilities of saccharinates of active pharmaceutical ingredients," Chem. Commun. 2005:1073-1075.

Bravo et al. "In-vitro studies of diclofenac sodium controlled-release from biopolymeric hydrophilic matrices." J. Pharm. Pharmaceut. Sci. 2002. 5:213-219.

Carlson et al., "The Plasma Pharmacokinetics of R-(+)-Lipoic Acid Administered as Sodium (R)-(+)-Lipoate to Healthy Human Subjects," Alternative Medicine Review, 2007;12(4):343-351.

Choulis et al., "Factors Effecting Drug Release From Inert Matrices. Part 1: Effects of Surfactants on the Release of Quinine Sulfate," Pharmazie, Apr. 1975, 30(4):233-236.

Christie et al., "Opioids, NSAIDs and 5-lipoxygenase inhibitors act synergistically in brain via arachidonic acid metabolism," Inflammation Research, Jan. 1999;48(1):1-4.

Daly et al., "The effect of anionic surfactants on the release of chlorpheniramine from a polymer matrix tablet," Int. J. Pharmaceutics, 1984,18(1-2):201-205.

Davis et al., "The use of gamma scintigraphy to simultaneously monitor the in vivo dissolution of drug from two formulations," J. Pharmacy & Pharmacology. Dec. 1983, 35(Suppl.) 105P.

El-Laithy, "Preparation and Physicochemical Characterization of Dioctyl Sodium Sulfosuccinate (Aerosol OT) Microemulsion for Oral Drug Delivery," AAPS PharmaSciTech, Mar. 31, 2003, 4(1):Article 11: 10 pgs.

Feely et al., "Influence of surfactants on drug release from hydroxypropylmethylcellulose matrices." Int. J. Pharmaceutics, Jan. 1988, 41(1-2):83-90.

Ferrero et al. "Towards elucidation of the drug release mechanism from compressed hydrophilic matrices mades of cellulose ethers. I. Pulse-field-gradient spin-echo NMR study of sodium salicylate diffusitivity in swollen hydrogels with respect to polymer matrix physical structure." 2008. J. Controlled Release. 128:71-79.

Ferrero Rodriguez et al. "Hydrophilic cellulose derivatives as drug delivery carriers: Influence of substitution type on the properties of compressed matrix tablets." In Handbook of Pharmaceutical Controlled Release Technology (ed. Donald L. Wise). CRC Press. 2000. 1:1-30.

Fingl et al., "General Principles," Chapter 1, The Pharmacological Basis of Therapeutics, New York, NY, 1975:1-46.

Ghosh et al. "Drug Delivery Through Osmotic Systems—An Overview", 2011. Journ. of App. Pharma Science. 01(02):38-49.

International Preliminary Report on Patentability issued Mar. 29, 2012, in regsrd to International Application No. PCT/US2009/069912, filed Dec. 31, 2009.

International Search Report / Written Opinion issued Nov. 25, 2010, in regard to International Patent Application No. PCT/US2009/069912, filed Dec. 31, 2009.

Kamel et al. "Pharmaceutical significance of cellulose: a review." eXPRESS Polymer Letters. 2008. 2:758-778.

Levina et al., "The Influence of Excipients on Drugs Release from Hydroxypropyl Methylcellulose Matrices," J. Pharmaceutical Sci., Nov. 2004, 93(11):2746-2754.

Matschiner et al., "Characterization of ion pair formation between erythromycin and lipophilic counter ions," Pharmazie, 1995. 50(7):462-464.

Pygall et al., "Mechanisms of drug release in citrate buffered HPMC matrices," Int. J. Pharmaceutics. 2009:370:110-120.

Raffa, "Pharmacology of oral combination analgesics: rational therapy for pain." J. Clin. Pharm. Ther., Aug. 2001; 26(4):257-264.

Ranga Rao et al. "Cellulose matrices for zero-order release of soluble drugs." 1988. Drug Dev. and Ind. Pharm. 14:2299-2320.

Rao et al., "Effect of Sodium Lauryl Sulfate on the Release of Rifampicin from Guar Gum Matrix," Indian J. Pharmaceutical Sci., Sep.-Oct. 2000, 62(5):404-406.

Rao, K.V. R.; Devi, K. P.; Buri, P. Cellulose matrices for zero-order release of soluble drugs. Drug Development and Industrial Pharmacy, 14 (15-17), 2299-2320.

Theeuwes et al., "Osmotic delivery systems for the beta-adrenoceptor antagonists metroprolol and exprenolol: design and evaluation of systems for once-daily administration." 1965. Br. J. Clin. Pharmac. 19:69S-76S.

Tiwari et al. "Controlled release formulation of tramadol hydrochloride using hydrophilic and hydrophobic matrix system." 2003. AAPS PharmSciTech. 4:1-6.

Wells et el., "Effect of anionic surfactants on the release of chlorpheniramine maleate from an inert, heterogeneous matrix," Drug Development and Industrial Pharmacy, 1992, 18(2):175-186.

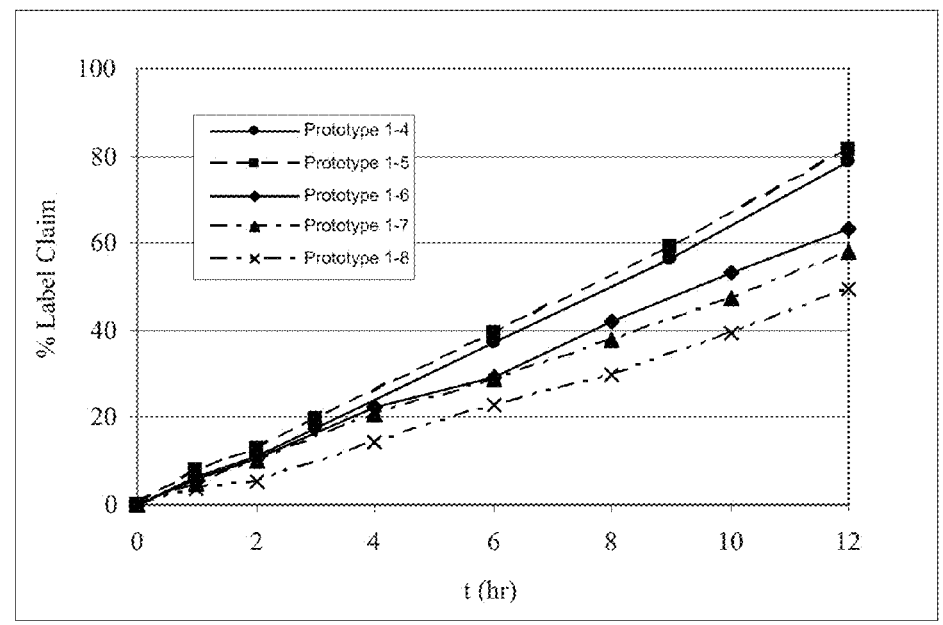
Figure 1. Dissolution of DXM in phosphate buffer
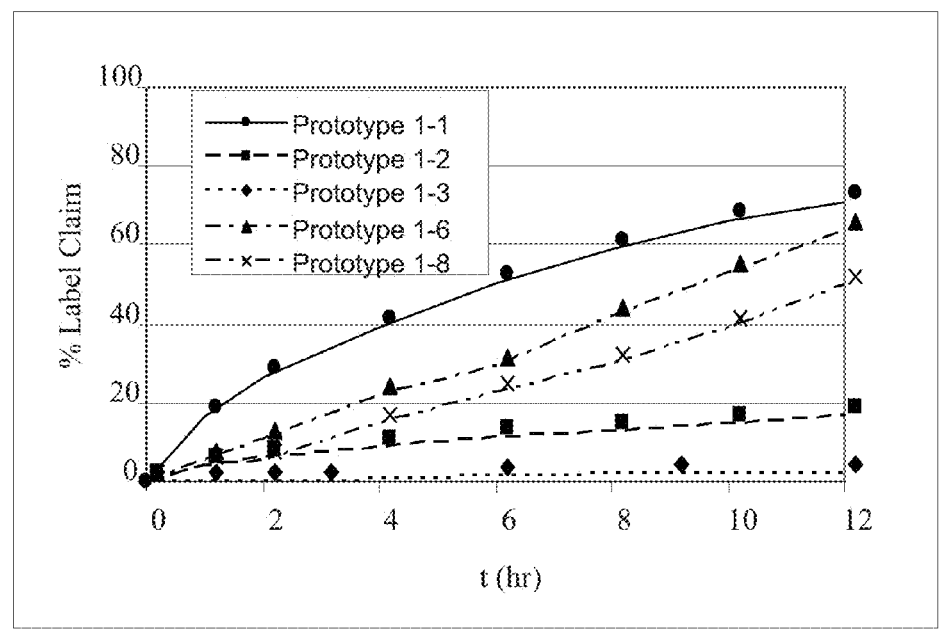
Figure 2. Dissolution of DXM in phosphate buffer

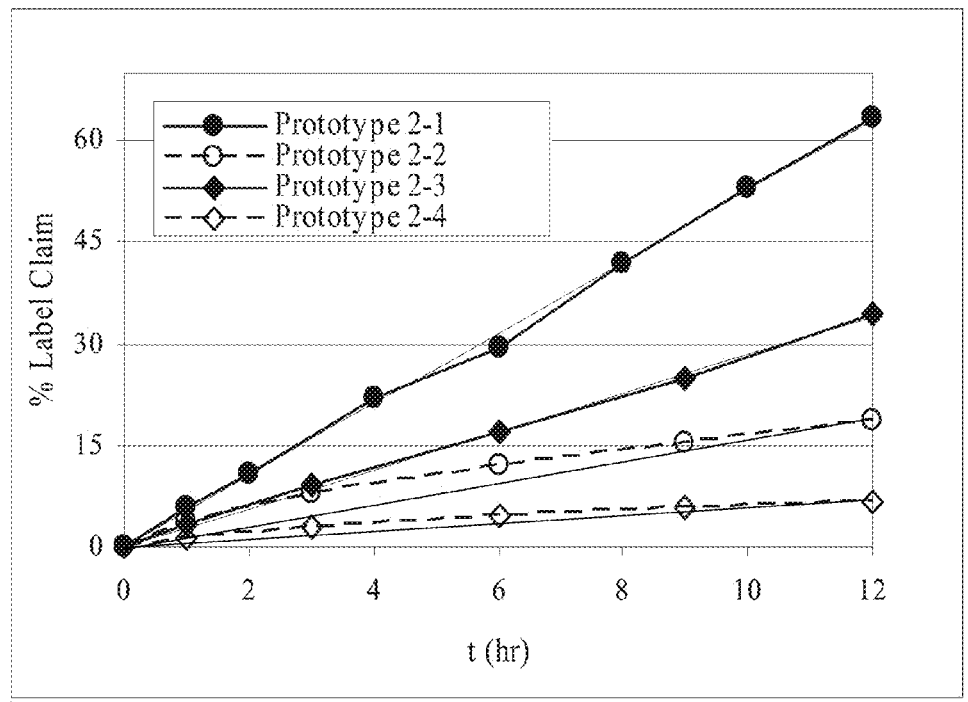
Figure 3. Dissolution of DXM in phosphate buffer
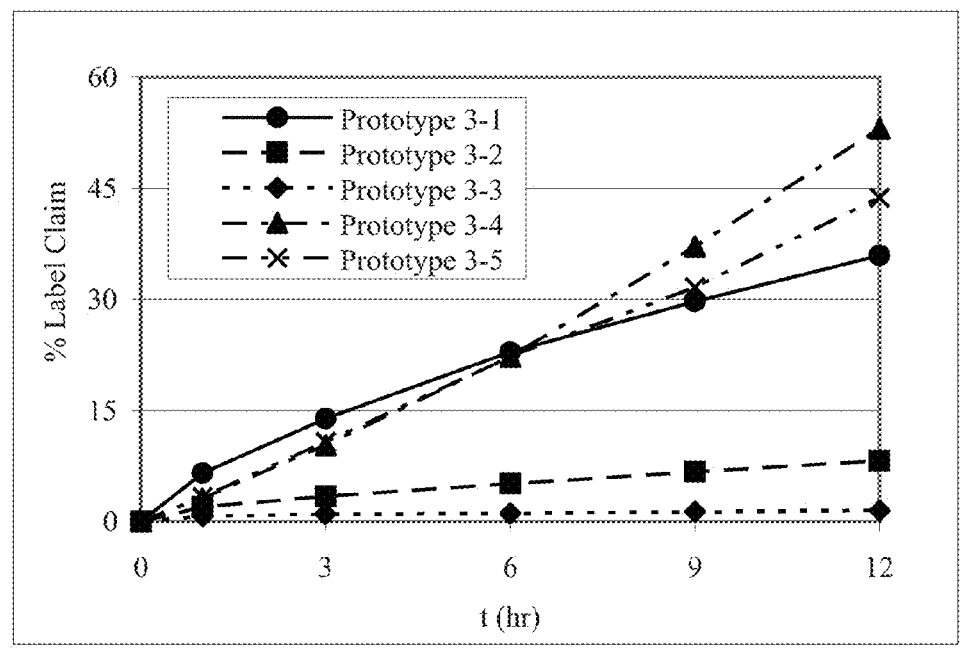
Figure 4. Dissolution of CBP in phosphate buffer

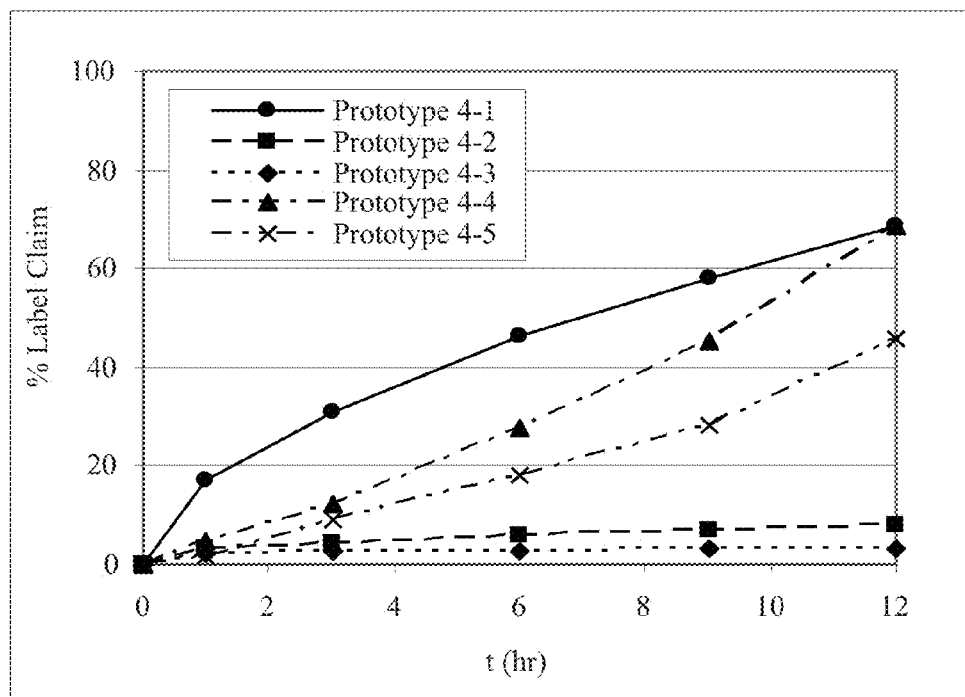
Figure 5. Dissolution of BTP in phosphate buffer
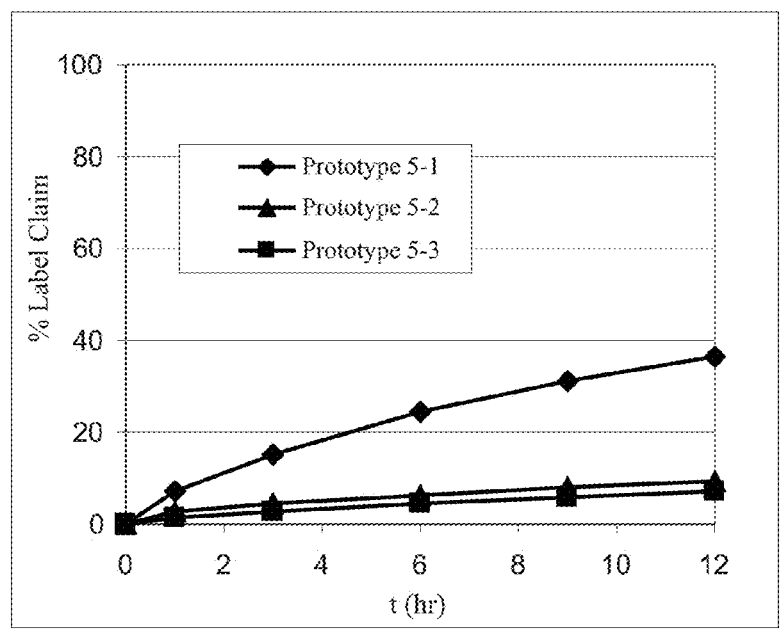
Figure 6. Dissolution of DXM in phosphate buffer

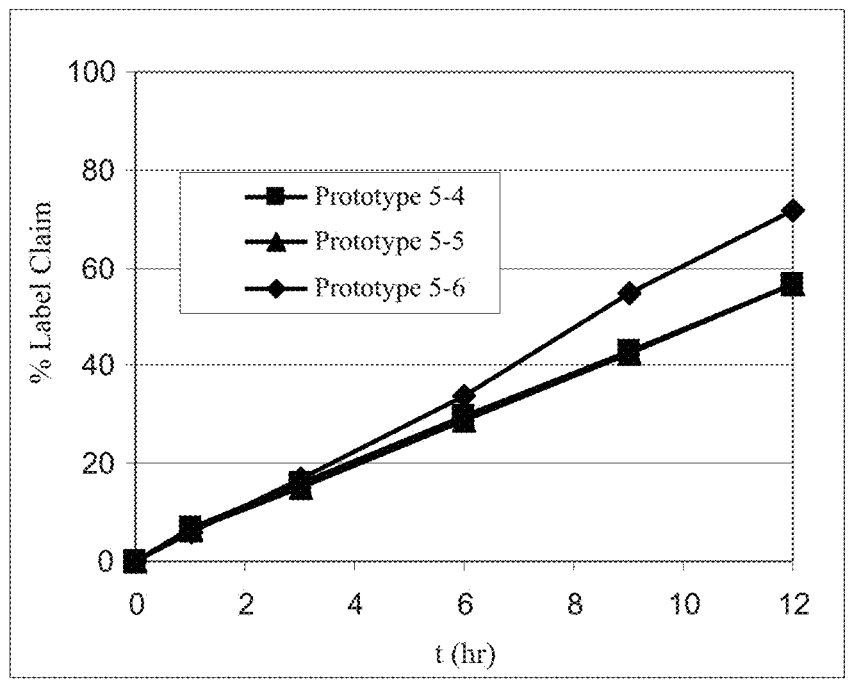
Figure 7. Dissolution of DXM in phosphate buffer
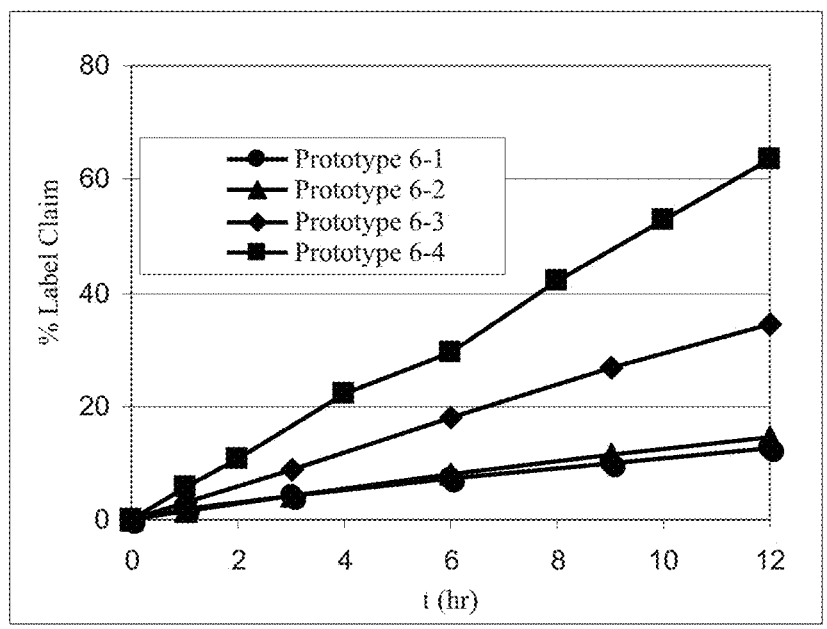
Figure 8. Dissolution of DXM in phosphate buffer Figure 9. Dissolution of DXM From Acidic and Hydroalcoholic Media (Prototype 7-1)
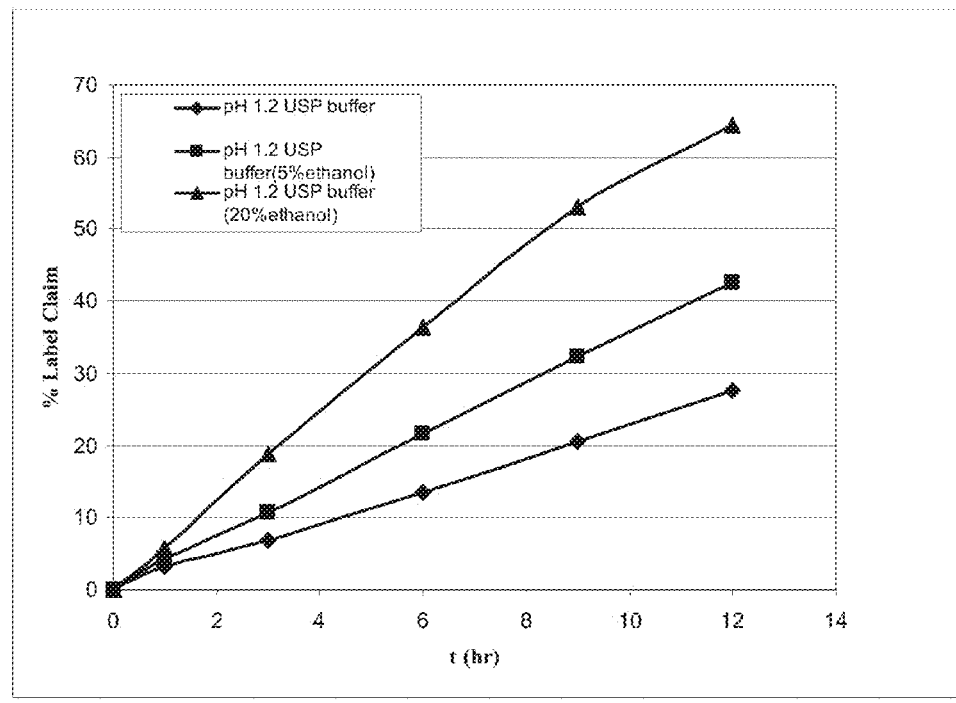
Figure 10. Dissolution of Amantadine Tablets in Phosphate Buffer
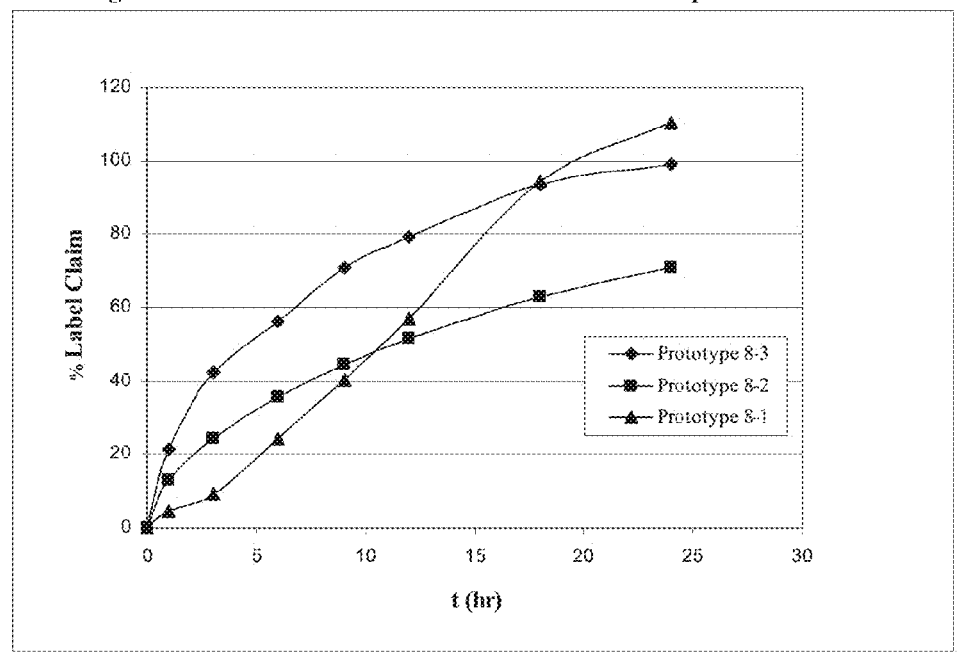

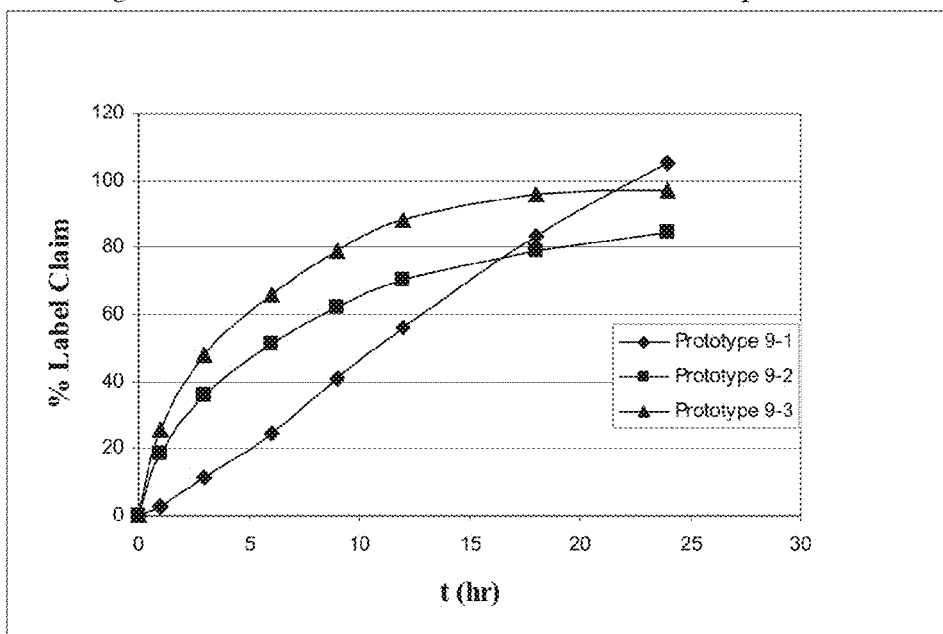
Figure 11. Dissolution of Memantine Tablets in Phosphate Buffer
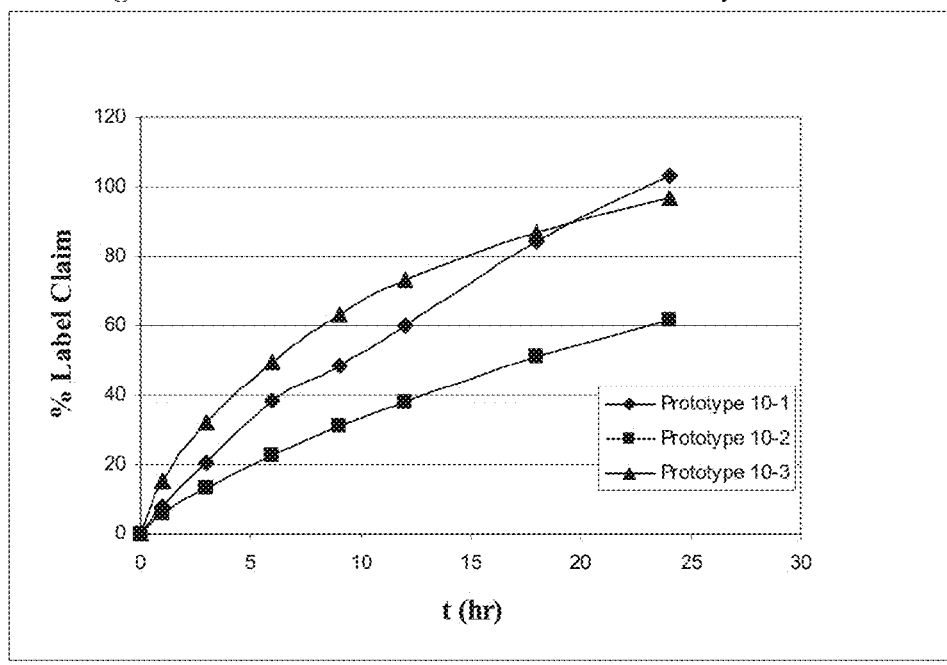
Figure 12. Dissolution of Ritodrine Tablets in Phosphate Buffer

SUSTAINED-RELEASED PRODUCT COMPRISING A COMBINATION OF A NON-OPIOID AMINE AND A NON-STEROIDAL, ANTI-INFLAMMATORY DRUG

CONTINUING APPLICATION DATA

This application is a continuation patent application of U.S. patent application Ser. No. 13/496,818, filed on Jun. 20, 2012, which is a U.S. National Stage Application of International Application No. PCT/US2009/069912, filed on Dec. 31, 2009, published in the English language on Mar. 24, 2011 as International Publication No. WO 2011/034554 A1, which claims the benefit of U.S. Provisional Application Ser. No. 61/243,391, filed Sep. 17, 2009. Attention is also directed to PCT Patent Application No. PCT/US2009/069902, filed Dec. 31, 2009, titled Opioid-Containing Oral Pharmaceutical Compositions and Methods, which claims the benefit of U.S. Provisional Application Ser. No. 61/141,765, filed Dec. 31, 2008. All of the above are incorporated by reference herein.

BACKGROUND

For many pharmacologically active compounds, immediate-release formulations are characterized by a short duration of action, typically necessitating frequent administrations in order to maintain therapeutic levels of the compounds in patients. Thus, there is a need for new oral pharmaceutical compositions that provide sustained release, and ideally zero-order release kinetics, and less frequent dosing.

SUMMARY

The present invention provides sustained-release oral pharmaceutical compositions and methods of use.

In one embodiment, the present invention provides a sustained-release oral pharmaceutical composition comprising within a single dosage form: a hydrophilic matrix; a therapeutically effective amount of a non-opioid amine-containing compound (including salts thereof) (wherein the amine group can be a primary, secondary, or tertiary amine, or combination thereof); and a salt of a non-steroidal anti-inflammatory drug (NSAID); wherein the amine-containing compound and the salt of an NSAID are within the hydrophilic matrix; wherein the composition exhibits a release profile of the amine-containing compound comprising a substantial portion that is representative of zero-order release kinetics (with respect to the amine-containing compound) under in vitro conditions.

In another embodiment, the present invention provides a sustained-release oral pharmaceutical composition comprising within a single dosage form: a hydrophilic matrix; a therapeutically effective amount of a non-opioid amine-containing compound (including salts thereof) (wherein the amine group can be a primary, secondary, or tertiary amine, or combination thereof); a salt of a non-steroidal anti-inflammatory drug (NSAID); and a pharmaceutically acceptable anionic surfactant; wherein the amine-containing compound, the salt of an NSAID, and the anionic surfactant are within the hydrophilic matrix. Preferred compositions exhibit a release profile of the amine-containing compound comprising a substantial portion that is representative of zero-order release kinetics under in vitro conditions.

The amine-containing compounds of the present invention include one or more amine groups. In certain preferred embodiments, the amine-containing compound comprises a tertiary amine. In certain embodiments, the amine-containing compound comprises a ring nitrogen that is a tertiary amine. In other preferred embodiments, the amine-containing compound comprises a tertiary amine or a secondary amine, or a combination thereof. Typically in the practice of the present invention, such amine-containing compounds are non-opioid compounds.

In a preferred embodiment, the present invention provides a sustained-release oral pharmaceutical composition comprising within a single dosage form: a hydrophilic matrix; a therapeutically effective amount of an amine-containing compound selected from the group consisting of dextromethorphan, cyclobenzaprine, benztropine (also sometimes referred to as benzatropine), salts thereof, and combinations thereof; and a salt of a non-steroidal anti-inflammatory drug (NSAID) selected from the group consisting of a salt of naproxen, diclofenac, ibuprofen, and combinations thereof; wherein the amine-containing compound and the salt of an NSAID are within the hydrophilic matrix; wherein the composition has a release profile of the amine-containing compound comprising a substantial portion that is representative of zero-order release kinetics under in vitro conditions.

In another preferred embodiment, the present invention provides a sustained-release oral pharmaceutical composition comprising within a single dosage form: a hydrophilic matrix; a therapeutically effective amount of an amine-containing compound selected from the group consisting of dextromethorphan, cyclobenzaprine, benztropine, salts thereof, and combinations thereof; a salt of a non-steroidal anti-inflammatory drug (NSAID) selected from the group consisting of a salt of naproxen, diclofenac, ibuprofen, and combinations thereof; and a pharmaceutically acceptable anionic surfactant selected from the group consisting of sodium lauryl sulfate, docusate sodium, docusate calcium, and combinations thereof; wherein the amine-containing compound, the salt of an NSAID, and the anionic surfactant are within the hydrophilic matrix. Preferred such compositions have a release profile of the amine-containing compound comprising a substantial portion that is representative of zero-order release kinetics under in vitro conditions.

In a preferred embodiment, the present invention provides a sustained-release oral pharmaceutical composition comprising within a single dosage form: a hydrophilic matrix comprising a hydroxypropyl methylcellulose; a therapeutically effective amount of an amine-containing compound selected from the group consisting of dextromethorphan, a salt thereof, and combinations thereof; and a salt of a non-steroidal anti-inflammatory drug (NSAID) selected from the group consisting of a salt of naproxen, and combinations thereof; wherein the amine-containing compound and the salt of an NSAID are within the hydrophilic matrix; wherein the composition exhibits a release profile of the amine-containing compound comprising a substantial portion that is representative of zero-order release kinetics under in vitro conditions.

In a preferred embodiment, the present invention provides a sustained-release oral pharmaceutical composition comprising within a single dosage form: a hydrophilic matrix comprising a hydroxypropyl methylcellulose; a therapeutically effective amount of an amine-containing compound selected from the group consisting of cyclobenzaprine, a salt thereof, and combinations thereof; and a salt of a non-steroidal anti-inflammatory drug (NSAID) selected from the group consisting of a salt of naproxen, and combinations thereof; wherein the amine-containing compound or salt thereof and the salt of an NSAID are within the hydrophilic matrix; wherein the composition exhibits a release profile of the amine-containing compound comprising a substantial portion that is representative of zero-order release kinetics under in vitro conditions.

In a preferred embodiment, the present invention provides a sustained-release oral pharmaceutical composition comprising within a single dosage form: a hydrophilic matrix comprising a hydroxypropyl methylcellulose; a therapeutically effective amount of an amine-containing compound selected from the group consisting of benztropine, a salt thereof, and combinations thereof; and a salt of a non-steroidal anti-inflammatory drug (NSAID) selected from the group consisting of a salt of naproxen, and combinations thereof; wherein the amine-containing compound and the salt of an NSAID are within the hydrophilic matrix; wherein the composition exhibits a release profile of the amine-containing compound comprising a substantial portion that is representative of zero-order release kinetics under in vitro conditions.

In a preferred embodiment, the present invention provides a sustained-release oral pharmaceutical composition comprising within a single dosage form: a hydrophilic matrix; a therapeutically effective amount of an amine-containing compound selected from the group consisting of dextromethorphan, cyclobenzaprine, benztropine, salts thereof, and combinations thereof; a salt of a non-steroidal anti-inflammatory drug (NSAID) selected from the group consisting of a salt of naproxen, diclofenac, ibuprofen, and combinations thereof; and a pharmaceutically acceptable anionic surfactant selected from the group consisting of sodium lauryl sulfate, docusate sodium, docusate calcium, and combinations thereof; wherein the amine-containing compound, the salt of an NSAID, and the anionic surfactant are within the hydrophilic matrix. Preferably, such composition exhibits a release profile of the amine-containing compound comprising a substantial portion that is representative of zero-order release kinetics under in vitro conditions.

In a preferred embodiment, the present invention provides a sustained-release oral pharmaceutical composition comprising within a single dosage form: a hydrophilic matrix comprising a hydroxypropyl methylcellulose; a therapeutically effective amount of an amine-containing compound selected from the group consisting of dextromethorphan, a salt thereof, and combinations thereof; a salt of a non-steroidal anti-inflammatory drug (NSAID) selected from the group consisting of a salt of naproxen, and combinations thereof; and a pharmaceutically acceptable anionic surfactant selected from the group consisting of docusate sodium, docusate calcium, and combinations thereof; wherein the amine-containing compound, the salt of an NSAID, and the anionic surfactant are within the hydrophilic matrix. Preferably, such composition exhibits a release profile of the amine-containing compound comprising a substantial portion that is representative of zero-order release kinetics under in vitro conditions.

In a preferred embodiment, the present invention provides a sustained-release oral pharmaceutical composition comprising within a single dosage form: a hydrophilic matrix comprising a hydroxypropyl methylcellulose; a therapeutically effective amount of an amine-containing compound selected from the group consisting of cyclobenzaprine, a salt thereof, and combinations thereof; a salt of a non-steroidal anti-inflammatory drug (NSAID) selected from the group consisting of a salt of naproxen, and combinations thereof; and a pharmaceutically acceptable anionic surfactant selected from the group consisting of docusate sodium, docusate calcium, and combinations thereof; wherein the amine-containing compound, the salt of an NSAID, and the anionic surfactant are within the hydrophilic matrix. Preferably, such composition exhibits a release profile of the amine-containing compound comprising a substantial portion that is representative of zero-order release kinetics under in vitro conditions.

In a preferred embodiment, the present invention provides a sustained-release oral pharmaceutical composition comprising within a single dosage form: a hydrophilic matrix comprising a hydroxypropyl methylcellulose; a therapeutically effective amount of an amine-containing compound selected from the group consisting of benztropine, a salt thereof, and combinations thereof; a salt of a non-steroidal anti-inflammatory drug (NSAID) selected from the group consisting of a salt of naproxen, and combinations thereof; and a pharmaceutically acceptable anionic surfactant selected from the group consisting of docusate sodium, docusate calcium, and combinations thereof; wherein the amine-containing compound, the salt of an NSAID, and the anionic surfactant are within the hydrophilic matrix. Preferably, such composition exhibits a release profile of the amine-containing compound comprising a substantial portion that is representative of zero-order release kinetics under in vitro conditions.

In a preferred embodiment, the present invention provides a method of providing a desired effect in a subject, the method administering to a subject a composition of any of the embodiments presented herein. In methods of the present invention, administering a composition of the present invention comprises administering once or twice per day, and often once per day.

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a composition comprising "a" salt of a non-steroidal anti-inflammatory drug can be interpreted to mean that the composition includes "one or more" non-steroidal anti-inflammatory drugs. Similarly, a composition comprising "a" pharmaceutically acceptable anionic surfactant can be interpreted to mean that the composition includes "one or more" pharmaceutically acceptable anionic surfactants.

As used herein, the term "or" is generally employed in its sense including "and/or" unless the content clearly dictates otherwise. The term "and/or" means one or all of the listed elements or a combination of any two or more of the listed elements.

Also herein, all numbers are assumed to be modified by the term "about" and preferably by the term "exactly." Notwithstanding that the numerical ranges and parameters setting forth the broad scope of the invention are approximations, the numerical values set forth in the specific examples are reported as precisely as possible. All numerical values, however, inherently contain certain errors necessarily resulting from the standard deviation found in their respective testing measurements.

Also herein, the recitations of numerical ranges by endpoints include all numbers subsumed within that range (e.g., 1 to 5 includes 1, 1.5, 2, 2.75, 3, 3.80, 4, 5, etc.). Where a range of values is "up to" a particular value, that value is included within the range.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIGS. 1-3 show dissolution profiles in phosphate buffer for certain dextromethorphan (DXM) formulations in accordance with embodiments of the present invention.

FIG. 4 shows dissolution profiles in phosphate buffer for certain cyclobenzaprine (CBP) formulation in accordance with embodiments of the present invention.

FIG. 5 shows dissolution profiles in phosphate buffer for certain benztropine (BTP) formulations in accordance with embodiments of the present invention.

FIG. 6-8 show dissolution profiles in phosphate buffer for certain DXM formulations in accordance with embodiments of the present invention.

FIG. 9 shows dissolution profiles in acidic and hydroalcoholic media for a DXM formulation in accordance with the present invention.

FIG. 10 shows dissolution profiles in phosphate buffer for amantadine tablet formulations in accordance with embodiments of the present invention.

FIG. 11 shows dissolution profiles in phosphate buffer for memantine tablet formulations in accordance with embodiments of the present invention.

FIG. 12 shows dissolution profiles in phosphate buffer for ritodrine tablet formulations in accordance with embodiments of the present invention.

DETAILED DESCRIPTION OF ILLUSTRATIVE EMBODIMENTS

The present invention provides sustained-release oral pharmaceutical compositions and methods of use. Preferably, such compositions are used for pain treatment, cough suppression, muscle relaxation, treatment of migraine headaches, spasms, convulsions, antihistamine effect, or other indications. Such compositions are in a single dosage form and include a pharmacologically active amine-containing compound (including salts thereof), a salt of a non-steroidal anti-inflammatory drug (NSAID), and a hydrophilic matrix. Certain embodiments also include a pharmaceutically acceptable anionic surfactant.

Herein, sustained-release compositions release the amine-containing compound over a period of time greater than 60 minutes. Preferred sustained-release formulations demonstrate at least 60%, and more preferably at least 80%, release of the amine-containing compound over a desired period (e.g., a period of 8 to 12 hours). If desired, however, the formulations of the present invention could be tailored to release the amine-containing compound over any period from 6 hours to 24 hours or longer.

Particularly preferred sustained-release compositions of the present invention demonstrate a zero-order release profile with respect to the amine-containing compound under in vitro conditions, such as when tested in accordance with appropriate United States Pharmacopeia test methods. Herein, "zero-order" with respect to the amine-containing compound (including salts thereof) means a relatively constant rate of release (i.e., exhibiting a substantially linear release profile over a period of time, preferably at least a few hours) of the amine-containing compound. Although a small portion (e.g., the initial 30-60 minutes) of the release profile may not be zero-order (e.g., as in a formulation containing an immediate-release coating, or a bilayer or multi-layer formulation comprising an immediate-release layer), a substantial portion (e.g., several hours), and preferably a major portion, of the release profile is representative of zero-order release kinetics.

Amine-Containing Compounds

The amine-containing compounds of the present invention are pharmacologically active compounds that include one or more amine groups (primary, secondary, tertiary amines, or combinations thereof). In certain preferred embodiments, the amine-containing compound comprises a tertiary amine. In certain embodiments, the amine-containing compound comprises a ring nitrogen that is a tertiary amine. In other preferred embodiments, the amine-containing compound comprises a tertiary amine or a secondary amine, or a combination thereof. In yet other embodiments, the amine-containing compound comprises two or more of a tertiary amine, a secondary amine, and a primary amine.

Typically, such amine-containing compounds are non-opioid compounds, which means that the compounds may be similar in structure to many opioids, but is not generally understood to bind to opioid receptors in the same way or at the same level as that of opioids. That is, such compounds are not typically characterized as opioids as they do not have any significant amount of opioid activity. Furthermore, the term "compound" as used herein includes salts thereof.

An opioid is a chemical substance that works by binding to opioid receptors, which are found principally in the central nervous system and the gastrointestinal tract. The receptors in these two organ systems mediate both the beneficial effects, and the undesirable side effects. There are three principal classes of opioid receptors, μ, κ, δ (mu, kappa, and delta), although up to seventeen have been reported, and include the ε, ι, λ, and ξ(Epsilon, Iota, Lambda and Zeta) receptors. There are three subtypes of μ receptor: $\mu_1$ and $\mu_2$, and the newly discovered $\mu_3$. Another receptor of clinical importance is the opioid-receptor-like receptor 1 (ORL1), which is involved in pain responses as well as having a major role in the development of tolerance to μ-opioid agonists used as analgesics. An opioid can have agonist characteristics, antagonist characteristics, or both. Compounds used in compositions of the present invention may be similar in structure to many opioids, but they are not generally understood to bind to opioid receptors in the same way or at the same level as that of opioids. That is, although compounds used in the present invention include one or more amine groups (which may be a primary, secondary, or tertiary amine), and certain compounds used in the present invention include a tertiary amine nitrogen, which may include a ring nitrogen, such compounds used herein are not typically characterized as opioids.

Various amine-containing compounds can be used in the practice of the invention. Each of these compounds includes a tertiary amine as shown, wherein the amine nitrogen may or may not be within a ring:

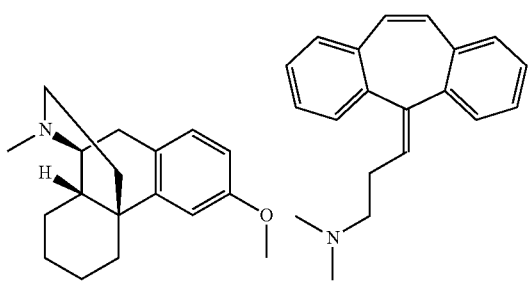

Dextromethorphan        Cyclobenzaprine

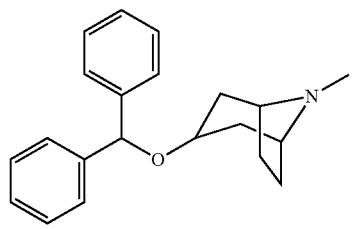

Benztropine

Dextromethorphan (DXM or DM, (+)-3-methoxy-17-methyl-9α,13α,14α-morphinan) is an antitussive drug used primarily as a cough suppressant, for the temporary relief of cough caused by minor throat and bronchial irritation (as commonly accompanies the common cold), as well as those resulting from inhaled irritants. Its mechanism of action is as an NMDA receptor antagonist.

Cyclobenzaprine (3-(5H-dibenzo[a,d]cyclohepten-5-ylidene)-N,N-dimethyl-1-propanamine) is a muscle relaxant that works in the central nervous system by blocking nerve impulses sent to the brain. It is used to treat skeletal muscle conditions such as pain and muscle spasms. The mechanism of action is unknown, although some research indicates that it inhibits the uptake of norepinephrine and blocks 5-HT2A and 5-HT2C receptors. It is also prescribed as a sleep-aid.

Benztropine ((3-endo)-3-(diphenylmethoxy)-8-methyl-8-azabicyclo[3.2.1]octane) is an anticholinergic drug principally used for the treatment of Parkinson's disease.

Other pharmacologically active amine-containing (non-opioid) compounds that may be useful in the practice of the present invention include the following:

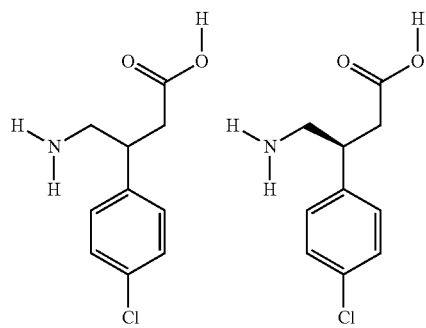

Baclofen    Arbaclofen
            (R-isomer of baclofen)

Ritodrine        Tizanidine

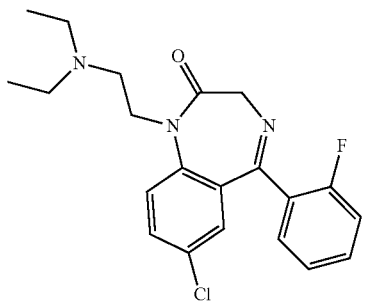

Flurazepam

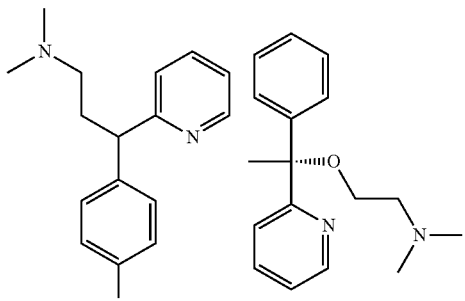

Chlorpheniramine        Doxylamine

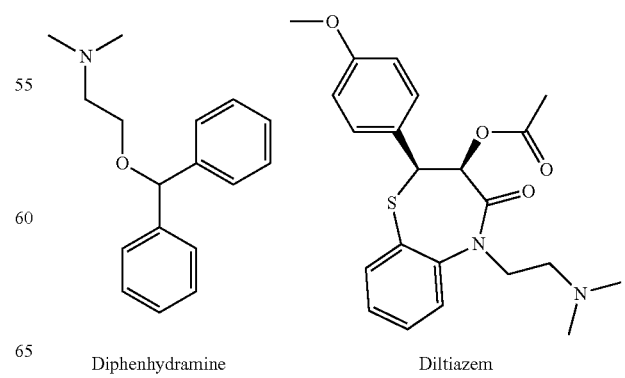

Diphenhydramine        Diltiazem

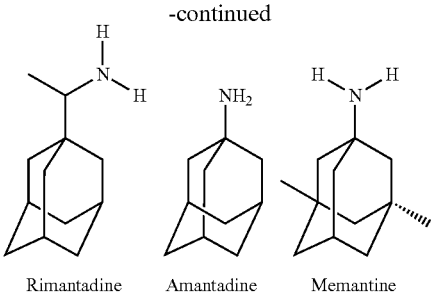

Rimantadine    Amantadine    Memantine

Such compounds function, for example, as muscle relaxants (baclofen, arbaclofen, ritodrine), antispasmodics (tizanidine), anticonvulsants (flurazepam), antihistamines (chlorpheniramine, doxylamine, and diphenhydramine), as treatment and/or prevention agents for migraine headaches (diltiazem), as antihypertensive agents (diltiazem), antivirals (rimantadine, amantadine), and/or as treatment of Parkinson's Disease (rimantadine, amantadine) or Alzheimer's Disease (memantine).

Mixtures of suitable amine-containing compounds may also be employed in the practice of the invention. That is, more than one pharmacologically active amine-containing compound may be incorporated into one dosage form.

The amine-containing compounds can be used if desired in a variety of salt forms including "pharmaceutically acceptable salts." Preparation of such salts is known to those skilled in pharmaceuticals. Examples of suitable pharmaceutically acceptable salts include, but are not limited to, hydrochlorides, bitartrates, acetates, naphthylates, tosylates, mesylates, besylates, succinates, palmitates, stearates, oleates, pamoates, laurates, valerates, hydrobromides, sulfates, methane sulfonates, tartrates, citrates, maleates, and the like, or combinations of any of the foregoing.

In some suitable embodiments, the amine-containing compound is selected from the group consisting of dextromethorphan (e.g., dextromethorphan hydrobromide), cyclobenzaprine (e.g., cyclobenzaprine hydrochloride), benztropine (e.g., benztropine mesylate) and combinations thereof. For certain embodiments, the amine-containing compound is dextromethorphan (particularly dextromethorphan hydrobromide). For certain embodiments, the amine-containing compound is cyclobenzaprine (particularly cyclobenzaprine hydrochloride). For certain embodiments, the amine-containing compound is benztropine (particularly benztropine mesylate).

An amine-containing compound is used herein in a therapeutically effective amount to provide a desired effect. Determination of a therapeutically effective amount will be determined by the condition being treated (e.g., pain, cough, spasms, migraine headaches, and the like) and on the target dosing regimen (e.g., once per day, twice per day). Determination of such an amount is well within the capability of those skilled in the art, especially in light of the detailed disclosure provided herein. For example, if the composition is used as a cough suppressant, the amount of an amine-containing compound would be that which is effective for suppressing a cough. If the composition is used to treat pain, for example, a therapeutically effective amount of an amine-containing compound is referred to herein as a "pain-reducing amount." Herein, this means an amount of compound effective to reduce or treat (i.e., prevent, alleviate, or ameliorate) symptoms over the desired time period. This amount can vary with each specific amine-containing compound depending on the potency of each. For example, the amount per single dosage form of the present invention may be 5 mg to 50 mg.

Salts of Non-Steroidal Anti-Inflammatory Drugs (NSAIDs)

Compositions of the present invention include one or more non-steroidal anti-inflammatory drugs, usually abbreviated to NSAIDs or NAIDs. These are drugs with analgesic, antipyretic and, in higher doses, anti-inflammatory effects.

NSAIDs are sometimes also referred to as non-steroidal anti-inflammatory agents/analgesics (NSAIAs) or non-steroidal anti-inflammatory medicines (NSAIMs). All NSAIDs as used herein are nonspecific COX inhibitors.

Surprisingly, in the practice of the present invention, salts of NSAIDs (but not the free bases) provide compositions with zero-order release kinetics with respect to the amine-containing compounds (including salts thereof).

There are roughly seven major classes of NSAIDs, including:

(1) salicylate derivatives, such as acetylsalicylic acid (aspirin), amoxiprin, benorylate/benorilate, choline magnesium salicylate, diflunisal, ethenzamide, faislamine, methyl salicylate, magnesium salicylate, salicyl salicylate, and salicylamide; a few structures of such compounds are as follows:

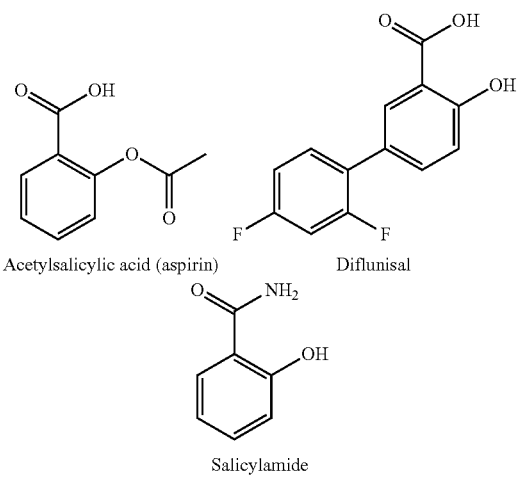

Acetylsalicylic acid (aspirin)    Diflunisal

Salicylamide (2) 2-aryl propionic acid derivatives, such as ibuprofen, ketoprofen, alminoprofen, carprofen, dexibuprofen, dexketoprofen, fenbufen, fenoprofen, flunoxaprofen, flurbiprofen, ibuproxam, ondoprofen, ketorolac, loxoprofen, naproxen, oxaprozin, pirprofen, suprofen, and tiaprofenic acid; a few structures of such compounds are as follows:

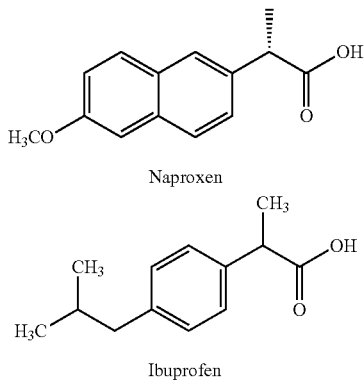

Naproxen

Ibuprofen

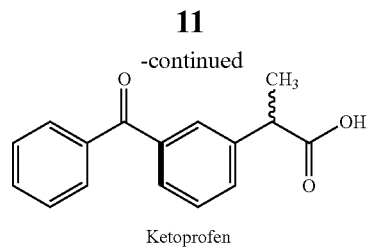

Ketoprofen

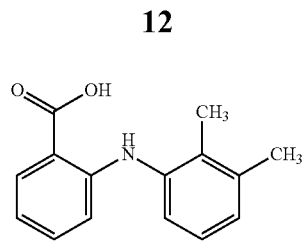

Mefenamic acid

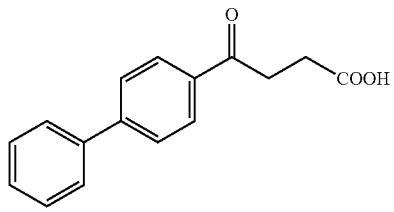

Fenbufen

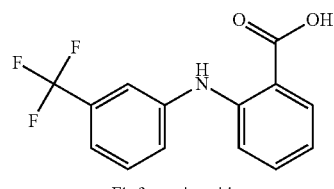

Flufenamic acid

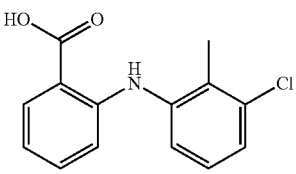

Tolfenamic acid (3) pyrazolidine derivatives, such as phenylbutazone, ampyrone, azapropazone, clofezone, kebuzone, metamizole, mofebutazone, oxyphenbutazone, phenazone, and sulfinpyrazone; a few structures of such compounds are as follows:

(5) oxicam derivatives, such as piroxicam, droxicam, lornoxicam, meloxicam, and tenoxicam; a few structures of such compounds are as follows:

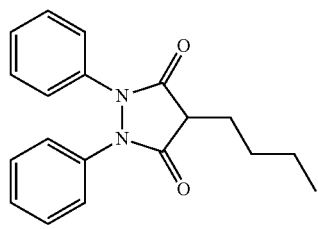

Phenylbutazone

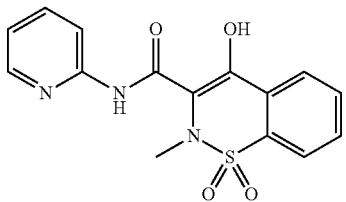

Piroxicam

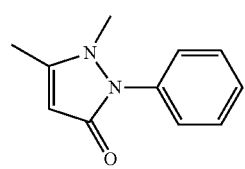

Phenazone

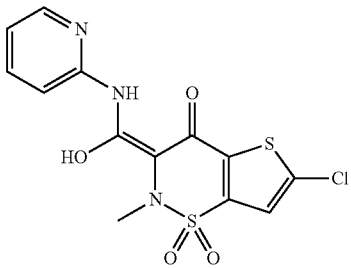

Lornoxicam

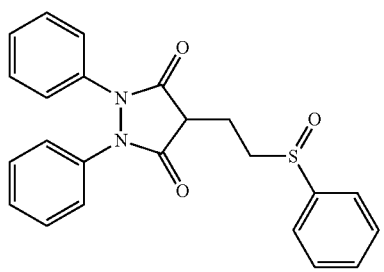

Sulfinpyrazone

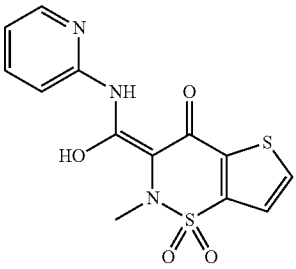

Tenoxicam (4) N-arylanthranilic acid (or fenamate) derivatives, such as mefenamic acid, flufenamic acid, meclofenamic acid, tolfenamic acid, and esters thereof; a few structures of such compounds are as follows:

(6) arylalkanoic acids, such as diclofenac, aceclofenac, acemethacin, alclofenac, bromfenac, etodolac, indomethacin, nabumetone, oxametacin, proglumetacin, sulindac (prodrug), and tolmetin; a few structures of such compounds are as follows:

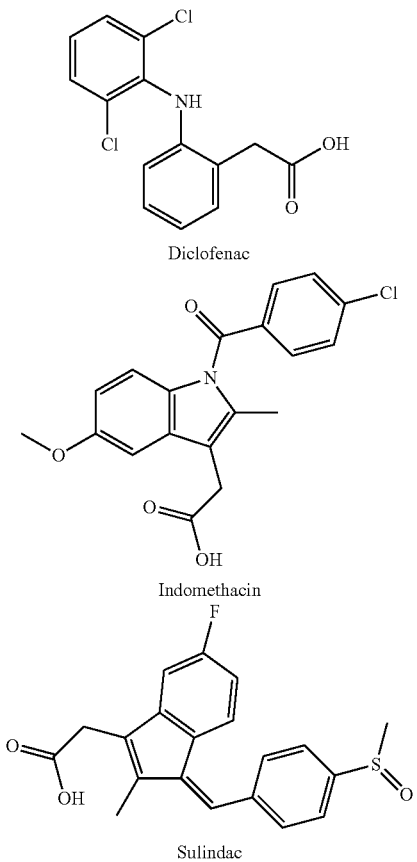

(7) indole derivatives, such as indomethacin, the structure of which is as follows:

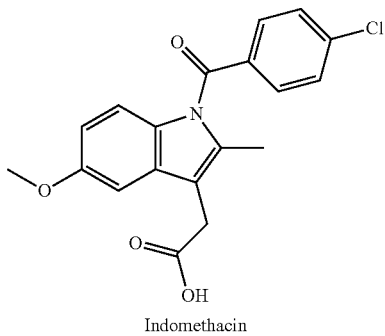 [SMILES: COc1ccc2c(c1)c(CC(=O)O)c(C)n2C(=O)c1ccc(Cl)cc1]

Although acetaminophen (paracetamol) is an analgesic and it is sometimes grouped with NSAIDs, it is not an NSAID (particularly for the purposes of the present invention) because it does not have any significant anti-inflammatory activity.

NSAIDs used in compositions of the present invention are pharmaceutically acceptable salts thereof. Typically, such salts include metal salts, such as sodium, calcium, or potassium salts. Salts such as bismuth salts, magnesium salts, or zinc salts may also be suitable. Various combinations of counterions and/or NSAID salts can be used if desired.

Preferred NSAID salts include a terminal carboxylic acid or terminal carboxylate group on the active moiety. In certain embodiments, the NSAID salts include a terminal carboxylic acid group on the active moiety. In certain embodiments, the NSAID salts include a terminal carboxylate group on the active moiety. Exemplary such NSAID salts are selected from the group consisting of a salicylate derivative, a 2-aryl propionic acid derivative, an N-arylanthranilic acid derivative, an aryl alkanoic acid, an indole derivative, and combinations thereof. Preferred NSAID salts include salts of 2-aryl propionic acid derivative (e.g., naproxen and ibuprofen), aryl alkanoic acids, or combinations thereof. Particularly preferred NSAID salts include naproxen sodium, ibuprofen sodium, diclofenac sodium, and combinations thereof. Structures of naproxen, diclofenac, and ibuprofen are as follows:

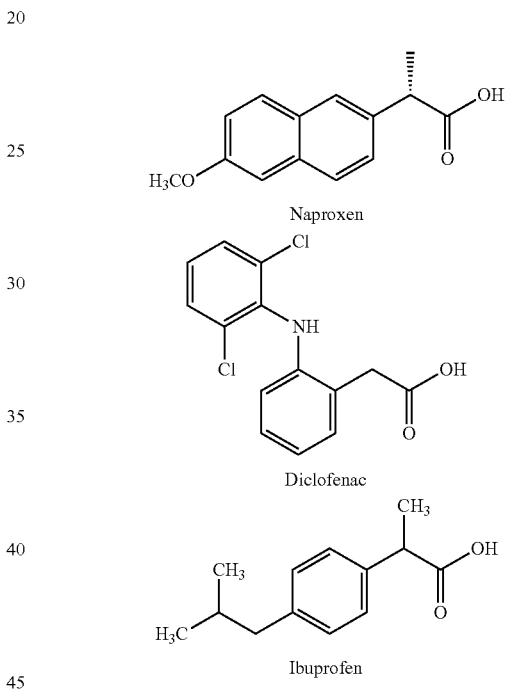

In preferred compositions, an NSAID salt is present in an amount to provide zero-order release kinetics with respect to the amine-containing compound under in vitro conditions. Such amount can be a sub-therapeutic amount or it can be a conventional therapeutic amount. Determination of such an amount is well within the capability of those skilled in the art, especially in light of the detailed disclosure provided herein. For example, naproxen sodium could be included in a single dosage form of the current invention at an amount of 220 mg to 750 mg (for a twice-per-day dosage form).

Pharmaceutically Acceptable Anionic Surfactants

Suitable pharmaceutically acceptable anionic surfactants could include, for example, monovalent alkyl carboxylates, acyl lactylates, alkyl ether carboxylates, N-acyl sarcosinates, polyvalent alkyl carbonates, N-acyl glutamates, fatty acid-polypeptide condensates, sulfur-containing surfactants (e.g., sulfuric acid esters, alkyl sulfates such as sodium lauryl sulfate (SLS), ethoxylated alkyl sulfates, ester linked sulfonates such as docusate sodium or dioctyl sodium succinate (DSS), and alpha olefin sulfonates), and phosphated ethoxylated alcohols. Preferred surfactants are on the GRAS ("Generally Recognized as Safe") list. Various combinations of pharmaceutically acceptable anionic surfactants can be used if desired.

In certain embodiments, the pharmaceutically acceptable anionic surfactant is a sulfur-containing surfactant, and particularly an alkyl sulfate, an ester-linked sulfonate, and combinations thereof. Preferred pharmaceutically acceptable anionic surfactants include sodium lauryl sulfate, docusate (i.e., dioctyl sulfosuccinate) sodium, docusate calcium, and combinations thereof. A particularly preferred anionic surfactant is docusate sodium. The structures of docusate sodium and sodium lauryl sulfate are as follows:

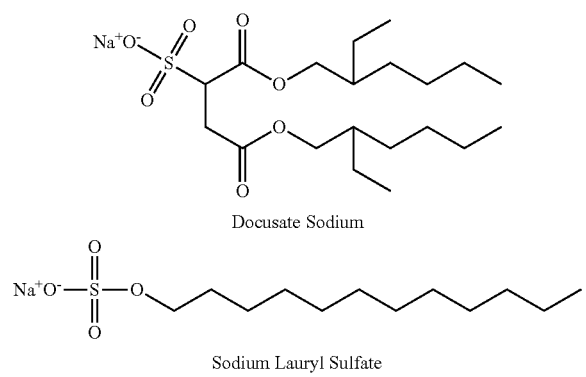

Docusate Sodium

Sodium Lauryl Sulfate

In preferred embodiments, a pharmaceutically acceptable anionic surfactant is present in compositions of the present invention in a release-modifying amount. A wide range of amounts can be used to tailor the rate and extent of release. Determination of such an amount is well within the capability of those skilled in the art, especially in light of the detailed disclosure provided herein.

In some embodiments, certain surfactants such as docusate can function as a stool softener when used at a therapeutic level; however, sub-therapeutic amounts can be used for release modification.

Such surfactants can be used for their abuse deterrence effects. For example, a surfactant could function as a nasal irritant, which would make crushing and inhaling the compositions undesirable. Also, a mixture of a non-opioid amine-containing compound and a surfactant (e.g., docusate) in a hydrophilic matrix is difficult to extract and separate into the individual components, and injection of the mixture is undesirable and/or unsafe.

Hydrophilic Matrix and Other Excipients

Compositions of the present invention include a hydrophilic matrix, wherein the amine-containing compound (including salt thereof), the salt of an NSAID, and the optional anionic surfactant are within (e.g., mixed within) the hydrophilic matrix. Such matrix preferably includes at least one hydrophilic polymeric compound. The hydrophilic polymeric compound preferably forms a matrix that releases the amine-containing compound (including a pharmaceutically acceptable salt thereof) at a sustained rate upon exposure to liquids. The rate of release of the amine-containing compound (including a pharmaceutically acceptable salt thereof) from the hydrophilic matrix typically depends, at least in part, on the amine-containing compound's partition coefficient between the components of the hydrophilic matrix and the aqueous phase within the gastrointestinal tract.

The sustained-release composition generally includes at least one hydrophilic polymeric compound in an amount of 10% to 90% by weight, preferably in an amount of 20% to 80% by weight, based on the total weight of the composition.

The hydrophilic polymeric compound may be any known in the art. Exemplary hydrophilic polymeric compounds include gums, cellulose ethers, acrylic resins, polyvinyl pyrrolidone, protein-derived compounds, and combinations thereof. Exemplary gums include heteropolysaccharide gums and homopolysaccharide gums, such as xanthan, tragacanth, pectins, acacia, karaya, alginates, agar, guar, hydroxypropyl guar, carrageenan, locust bean gums, and gellan gums. Exemplary cellulose ethers include hydroxyalkyl celluloses and carboxyalkyl celluloses. Preferred cellulose ethers include hydroxyethyl celluloses, hydroxypropyl celluloses, hydroxypropyl methylcelluloses, carboxymethylcelluloses, and mixtures thereof. Exemplary acrylic resins include polymers and copolymers of acrylic acid, methacrylic acid, methyl acrylate, and methyl methacrylate. Various combinations of hydrophilic compounds can be used for various effects.

In some embodiments, the hydrophilic compound is preferably a cellulose ether. Exemplary cellulose ethers include those commercially available under the trade designation METHOCEL Premium from Dow Chemical Co. Such methylcellulose and hypromellose (i.e., hydroxypropyl methylcellulose) products are a broad range of water-soluble cellulose ethers that enable pharmaceutical developers to create formulas for tablet coatings, granulation, sustained release, extrusion, and molding. For certain embodiments, the cellulose ether comprises a hydroxypropyl methylcellulose.

Varying the types of cellulose ethers can impact the release rate. For example, varying the types of METHOCEL cellulose ethers, which have different viscosities of 2% solutions in water (METHOCEL K4M Premium hypromellose 2208 (19-24% methoxy content; 7-12% hydroxypropyl content; 3,000-5,600 cps of a 2% solution in water); METHOCEL K15M Premium hypromellose 2208 (19-24% methoxy content; 7-12% hydroxypropyl content; 11,250-21,000 cps of a 2% solution in water); and METHOCEL K100M Premium hypromellose 2208 (19-24% methoxy content; 7-12% hydroxypropyl content; 80,000-120,000 cps of a 2% solution in water)) can help tailor release rates.

Compositions of the present invention can also include one or more excipients such as lubricants, glidants, flavorants, coloring agents, stabilizers, binders, fillers, disintegrants, diluents, suspending agents, viscosity enhancers, wetting agents, buffering agents, control release agents, crosslinking agents, preservatives, and the like. Such compounds are well known in the art of drug release and can be used in various combinations.

One particularly useful excipient that can form at least a portion of a composition of the present invention is a binder that includes, for example, a cellulose such as microcrystalline cellulose. An exemplary microcrystalline cellulose is that available under the trade designation AVICEL PH (e.g., AVICEL PH-101, AVICEL PH-102, AVICEL PH-301, AVICEL PH-302, and AVICEL RC-591) from FMC BioPolymers. The sustained-release composition generally includes at least one microcrystalline cellulose in an amount of 3 wt-% to 50 wt-%, based on the total weight of the composition.

Other additives can be incorporated into compositions of the present invention to further modify the rate and extent of release. For example, a non-pharmacologically active amine, such as tromethamine, triethanolamine, betaine, benzathine, or erbumine could be included in the compositions of the present invention to further modify the release rate.

Compositions of the present invention can optionally include compounds that function as abuse deterrents. For example, compounds that cause nausea could be added to the formulation containing, for example, DXM, to prevent abusers from taking more than the intended dose. These components are added to the formulation at sub-therapeutic levels, such that no adverse effects are realized when the correct dose is taken.

Also, compositions of the present invention can include an aversive agent such as a dye (e.g., one that stains the mucous membrane of the nose and/or mouth) that is released when the dosage form is tampered with and provides a noticeable color or dye which makes the act of abuse visible to the abuser and to others such that the abuser is less likely to inhale, inject, and/or swallow the tampered dosage form. Examples of various dyes that can be employed as the aversive agent, including for example, and without limitation, FD&C Red No. 3, FD&C Red No. 20, FD&C Yellow No. 6, FD&C Blue No. 1, FD&C Blue No. 2, FD&C Green No. 1, FD&C Green No. 3, FD&C Green No. 5, FD&C Red No. 30, D&C Orange No. 5, D&C Red No. 8, D&C Red No. 33, caramel, and ferric oxide, red, other FD&C dyes and lakes, and natural coloring agents such as grape skin extract, beet red powder, beta-carotene, annato, carmine, turmeric, paprika, and combinations thereof.

The sustained-release compositions of the present invention may also include one or more hydrophobic polymers. The hydrophobic polymers may be used in an amount sufficient to slow the hydration of the hydrophilic compound without disrupting it. For example, the hydrophobic polymer may be present in an amount of 0.5% to 20% by weight, based on the total weight of the composition.

Exemplary hydrophobic polymers include alkyl celluloses (e.g., $C_{1-6}$ alkyl celluloses, carboxymethylcellulose, ethylcellulose), other hydrophobic cellulosic materials or compounds (e.g., cellulose acetate phthalate, hydroxypropylmethylcellulose phthalate), polyvinyl acetate polymers (e.g., polyvinyl acetate phthalate), polymers or copolymers derived from acrylic and/or methacrylic acid esters, zein, waxes (e.g., carnauba wax), shellac, hydrogenated vegetable oils, and combinations thereof.

Pharmaceutical Compositions

Pharmaceutical compositions of the present invention are single dosage forms that can be in a form capable of providing sustained release of an amine-containing compound. Herein, a "single dosage form" refers to the components of the composition included within one physical unit (e.g., one tablet), whether it be in a uniform matrix, a multilayered construction, or some other configuration. Most commonly, this includes a tablet, which can include molded tablets, compressed tablets, or freeze-dried tablets. Other possible solid forms include pills, pellets, particulate forms (e.g., beads, powders, granules), and capsules (e.g., with particulate therein).

A single dosage form can be a coated dosage form with, for example, an outer layer of an immediate-release (IR) material (e.g., an amine-containing compound, an NSAID, or both, a release-modifying agent, a film coating for taste masking or for ease of swallowing, or the like), with a sustained-release (SR) core. Typically, such coated formulations do not demonstrate zero-order release kinetics during an initial immediate-release phase, but preferably demonstrate zero-order release kinetics with respect to the amine-containing compound during the dissolution of the sustained-release core.

A single dosage form can be incorporated into a multi-layered dosage form (e.g., tablet). For example, a bilayer tablet could be formulated to include a layer of a conventional immediate-release matrix and a layer of a sustained-release composition of the present invention. Optionally, a multi-layered dosage form could be coated.

Pharmaceutical compositions for use in accordance with the present invention may be formulated in conventional manner to incorporate one or more physiologically acceptable carriers comprising excipients and auxiliaries. Compositions of the invention may be formulated as tablets, pills, capsules, and the like, for oral ingestion by a patient to be treated.

Pharmaceutical compositions of the present invention may be manufactured in a manner that is itself known, e.g., by means of conventional mixing, granulating, encapsulating, entrapping, or tabletting processes.

Pharmaceutical compositions suitable for use in the present invention include compositions where the ingredients are contained in an amount effective to achieve its intended purpose. The exact formulation, route of administration, and dosage for the pharmaceutical compositions of the present invention can be chosen by the individual physician in view of the patient's condition. (See, e.g., Fingl et al. in "The Pharmacological Basis of Therapeutics", Ch. 1, p. 1 (1975)). The exact dosage will be determined on a drug-by-drug basis, in most cases. Dosage amount and interval may be adjusted individually to provide plasma levels of the active ingredients/moieties that are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. The amount of composition administered will, of course, be dependent on the subject being treated, on the subject's weight, the severity of the symptoms (e.g., pain, cough, spasms, etc.), the manner of administration, and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert.

It will be understood by those of skill in the art that numerous and various modifications can be made without departing from the spirit of the present invention. Therefore, it should be clearly understood that the forms of the present invention are illustrative only and are not intended to limit the scope of the present invention.

EXEMPLARY EMBODIMENTS OF THE INVENTION

1. A sustained-release oral pharmaceutical composition comprising within a single dosage form:
   a hydrophilic matrix;
   a therapeutically effective amount of a non-opioid amine-containing compound; and a salt of a non-steroidal anti-inflammatory drug (NSAID);
wherein the amine-containing compound and the salt of an NSAID are within the hydrophilic matrix; and
wherein the composition exhibits a release profile of the amine-containing compound comprising a substantial portion that is representative of zero-order release kinetics under in vitro conditions.

2. A sustained-release oral pharmaceutical composition comprising within a single dosage form:
a hydrophilic matrix;
a therapeutically effective amount of a non-opioid amine-containing compound;
a salt of a non-steroidal anti-inflammatory drug (NSAID); and
a pharmaceutically acceptable anionic surfactant;
wherein the amine-containing compound, the salt of an NSAID, and the anionic surfactant are within the hydrophilic matrix.

3. The composition of embodiment 2 which exhibits a release profile of the amine-containing compound comprising a substantial portion that is representative of zero-order release kinetics under in vitro conditions.

4. The composition of any one of embodiments 1 through 3 wherein the amine group comprises a secondary amine, a tertiary amine, a primary amine, or combination thereof 5. The composition of embodiment 4 wherein the amine-containing compound comprises a tertiary amine 6. The composition of embodiment 4 wherein the amine-containing compound comprises a primary amine.

7. The composition of embodiment 4 wherein the amine-containing compound comprises a secondary amine 8. The composition of any one of embodiments 1 through 4 wherein the amine-containing compound is selected from the group consisting of dextromethorphan, cyclobenzaprine, benztropine, baclofen, arbaclofen, ritodrine, tizanidine, flurazepam, chlorpheniramine, doxylamine, diphenhydramine, diltiazem, rimantadine, amantadine, memantine, and combinations thereof 9. The composition of any one of embodiments 1 through 8 wherein the amine-containing compound salt comprises a hydrochloride, a bitartrate, an acetate, a naphthylate, a tosylate, a mesylate, a besylate, a succinate, a palmitate, a stearate, an oleate, a pamoate, a laurate, a valerate, a hydrobromide, a sulfate, a methane sulfonate, a tartrate, a citrate, a maleate, or a combination of the foregoing.

10. The composition of embodiment 8 or embodiment 9 wherein the amine-containing compound is selected from the group consisting of dextromethorphan, cyclobenzaprine, benztropine, ritodrine, memantine, amantadine, salts thereof, and combinations thereof 11. The composition of embodiment 8 wherein the amine-containing compound is selected from the group consisting of dextromethorphan hydrobromide, cyclobenzaprine hydrochloride, benztropine mesylate, ritodrine hydrochloride, memantine hydrochloride, amantadine hydrochloride, and combinations thereof 12. The composition of any one of embodiments 8 through 10 wherein the amine-containing compound is selected from the group consisting of dextromethorphan, a salt thereof, and combinations thereof 13. The composition of embodiment 12 wherein the amine-containing compound comprises dextromethorphan hydrobromide.

14. The composition of any one of embodiments 8 through 10 wherein the amine-containing compound is selected from the group consisting of cyclobenzaprine, a salt thereof, and combinations thereof.

15. The composition of embodiment 14 wherein the amine-containing compound comprises cyclobenzaprine hydrochloride.

16. The composition of any one of embodiments 8 through 10 wherein the amine-containing compound is selected from the group consisting of benztropine, a salt thereof, and combinations thereof.

17. The composition of embodiment 16 wherein the amine-containing compound comprises benztropine mesylate.

18. The composition of any one of embodiments 8 through 10 wherein the amine-containing compound is selected from the group consisting of ritodrine, a salt thereof, and combinations thereof.

19. The composition of embodiment 18 wherein the amine-containing compound comprises ritodrine hydrochloride.

20. The composition of any one of embodiments 8 through 10 wherein the amine-containing compound is selected from the group consisting of memantine, a salt thereof, and combinations thereof.

21. The composition of embodiment 20 wherein the amine-containing compound comprises memantine hydrochloride.

22. The composition of any one of embodiments 8 through 10 wherein the amine-containing compound is selected from the group consisting of amantadine, a salt thereof, and combinations thereof.

23. The composition of embodiment 18 wherein the amine-containing compound comprises amantadine hydrochloride.

24. The composition of any one of the preceding embodiments wherein the NSAID salt is selected from the group consisting of a salicylate derivative, a 2-aryl propionic acid derivative, a pyrazolidine derivative, an N-arylanthranilic acid derivative, an oxicam derivative, an arylalkanoic acid, an indole derivative, and combinations thereof 25. The composition of embodiment 24 wherein the NSAID salt comprises a terminal carboxylic acid group or terminal carboxylate group.

26. The composition of embodiment 25 wherein the NSAID salt is selected from the group consisting of a salicylate derivative, a 2-aryl propionic acid derivative, an N-arylanthranilic acid derivative, an aryl alkanoic acid, an indole derivative, and combinations thereof 27. The composition of embodiment 26 wherein the NSAID salt is a 2-aryl propionic acid derivative, an aryl alkanoic acid, or combinations thereof 28. The composition of embodiment 27 wherein the NSAID salt is selected from the group consisting of a salt of naproxen, diclofenac, ibuprofen, and combinations thereof 29. The composition of embodiment 28 wherein the NSAID salt is selected from the group consisting of naproxen sodium, diclofenac sodium, ibuprofen sodium, and combinations thereof 30. The composition of any one of embodiments 2 through 29, as they depend on embodiment 2, wherein the pharmaceutically acceptable anionic surfactant is selected from the group consisting of monovalent alkyl carboxylates, acyl lactylates, alkyl ether carboxylates, N-acyl sarcosinates, polyvalent alkyl carbonates, N-acyl glutamates, fatty acid-polypeptide condensates, sulfur-containing surfactants, phosphated ethoxylated alcohols, and combinations thereof 31. The composition of embodiment 30 wherein the pharmaceutically acceptable anionic surfactant is a sulfur-containing surfactant.

32. The composition of embodiment 31 wherein the sulfur-containing surfactant is selected from the group consisting of an alkyl sulfate, an ester-linked sulfonate, and combinations thereof 33. The composition of embodiment 32 wherein the pharmaceutically acceptable anionic surfactant is selected from the group consisting of sodium lauryl sulfate, docusate sodium, docusate calcium, and combinations thereof 34. The composition of embodiment 33 wherein the pharmaceutically acceptable anionic surfactant is docusate sodium.

35. The composition of any one of the preceding embodiments wherein the NSAID salt is present in an amount effective to provide zero-order release kinetics under in vitro conditions.

36. The composition of any one of the preceding embodiments wherein the pharmaceutically acceptable anionic surfactant is present in a release-modifying amount.

37. The composition of any one of the preceding embodiments wherein the single dosage form is a tablet form.

38. The composition of embodiment 37 wherein the single dosage form tablet comprises a unitary matrix.

39. The composition of embodiment 37 wherein the single dosage form tablet comprises a multilayer tablet.

40. The composition of embodiment 39 wherein the single dosage form comprises an outer layer of an immediate-release (IR) material and a sustained-release (SR) core.

41. The composition of embodiment 40 wherein the IR material comprises an amine-containing compound, an NSAID, or both.

42. The composition of any one of the previous embodiments wherein the hydrophilic matrix comprises at least one hydrophilic polymeric compound selected from the group consisting of a gum, a cellulose ether, an acrylic resin, a polyvinyl pyrrolidone, a protein-derived compound, and combinations thereof 43. The composition of embodiment 42 wherein the hydrophilic polymeric compound comprises a cellulose ether.

44. The composition of embodiment 43 wherein the cellulose ether comprises a hydroxyalkyl cellulose, a carboxyalkyl cellulose, and combinations thereof 45. The composition of embodiment 44 wherein the cellulose ether comprises a methylcellulose, a hydroxypropyl methylcellulose, and combinations thereof 46. The composition of embodiment 45 wherein the cellulose ether comprises a hydroxypropyl methylcellulose.

47. The composition of any one of the previous embodiments further including one or more excipients.

48. The composition of embodiment 47 wherein the excipients comprise lubricants, glidants, flavorants, coloring agents, stabilizers, binders, fillers, disintegrants, diluents, suspending agents, viscosity enhancers, wetting agents, buffering agents, control release agents, crosslinking agents, preservatives, and combinations thereof 49. The composition of embodiment 48 comprising a binder.

50. The composition of embodiment 49 wherein the binder comprises a microcrystalline cellulose.

51. A sustained-release oral pharmaceutical composition comprising within a single dosage form:
a hydrophilic matrix;
a therapeutically effective amount of an amine-containing compound selected from the group consisting of dextromethorphan, cyclobenzaprine, benztropine, ritodrine, memantine, amantadine, salts thereof, and combinations thereof; and
a salt of a non-steroidal anti-inflammatory drug (NSAID) selected from the group consisting of a salt of naproxen, diclofenac, ibuprofen, and combinations thereof;
wherein the amine-containing compound and the salt of an NSAID are within the hydrophilic matrix; and
wherein the composition exhibits a release profile of the amine-containing compound comprising a substantial portion that is representative of zero-order release kinetics under in vitro conditions.

52. The composition of embodiment 51 wherein the amine-containing compound is selected from the group consisting of dextromethorphan, a salt thereof, and combinations thereof 53. The composition of embodiment 52 wherein the amine-containing compound comprises dextromethorphan hydrobromide.

54. The composition of embodiment 51 wherein the amine-containing compound is selected from the group consisting of cyclobenzaprine, a salt thereof, and combinations thereof 55. The composition of embodiment 54 wherein the amine-containing compound comprises cyclobenzaprine hydrochloride.

56. The composition of embodiment 51 wherein the amine-containing compound is selected from the group consisting of benztropine, a salt thereof, and combinations thereof 57. The composition of embodiment 56 wherein the amine-containing compound comprises benztropine mesylate.

58. The composition of embodiment 51 wherein the amine-containing compound is selected from the group consisting of ritodrine, a salt thereof, and combinations thereof 59. The composition of embodiment 58 wherein the amine-containing compound comprises ritodrine hydrochloride.

60. The composition of embodiment 51 wherein the amine-containing compound is selected from the group consisting of memantine, a salt thereof, and combinations thereof 61. The composition of embodiment 60 wherein the amine-containing compound comprises memantine hydrochloride.

62. The composition of embodiment 51 wherein the amine-containing compound is selected from the group consisting of amantadine, a salt thereof, and combinations thereof 63. The composition of embodiment 62 wherein the amine-containing compound comprises amantadine hydrochloride.

64. The composition of any one of embodiments 51 through 63 wherein the NSAID salt is selected from the group consisting of naproxen sodium, diclofenac sodium, ibuprofen sodium, and combinations thereof 65. The composition of any one of embodiments 51 through 64 wherein the hydrophilic polymeric compound comprises a cellulose ether.

66. The composition of embodiment 65 wherein the cellulose ether comprises a hydroxyalkyl cellulose, a carboxyalkyl cellulose, and combinations thereof 67. The composition of embodiment 65 wherein the cellulose ether comprises a methylcellulose, a hydroxypropyl methylcellulose, and combinations thereof 68. The composition of embodiment 65 wherein the cellulose ether comprises a hydroxypropyl methylcellulose.

69. A sustained-release oral pharmaceutical composition comprising within a single dosage form:
a hydrophilic matrix comprising a hydroxypropyl methylcellulose;

23 a therapeutically effective amount of an amine-containing compound selected from the group consisting of dextromethorphan, a salt thereof, and combinations thereof; and a salt of a non-steroidal anti-inflammatory drug (NSAID) selected from the group consisting of a salt of naproxen, and combinations thereof;

wherein the amine-containing compound and the salt of an NSAID are within the hydrophilic matrix; and wherein the composition exhibits a release profile of the amine-containing compound comprising a substantial portion that is representative of zero-order release kinetics under in vitro conditions.

70. A sustained-release oral pharmaceutical composition comprising within a single dosage form:

a hydrophilic matrix comprising a hydroxypropyl methylcellulose;

a therapeutically effective amount of an amine-containing compound selected from the group consisting of cyclobenzaprine, a salt thereof, and combinations thereof; and a salt of a non-steroidal anti-inflammatory drug (NSAID) selected from the group consisting of a salt of naproxen, and combinations thereof;

wherein the amine-containing compound and the salt of an NSAID are within the hydrophilic matrix; and wherein the composition exhibits a release profile of the amine-containing compound comprising a substantial portion that is representative of zero-order release kinetics under in vitro conditions.

71. A sustained-release oral pharmaceutical composition comprising within a single dosage form:

a hydrophilic matrix comprising a hydroxypropyl methylcellulose;

a therapeutically effective amount of an amine-containing compound selected from the group consisting of benztropine, a salt thereof, and combinations thereof; and a salt of a non-steroidal anti-inflammatory drug (NSAID) selected from the group consisting of a salt of naproxen, and combinations thereof;

wherein the amine-containing compound and the salt of an NSAID are within the hydrophilic matrix; and wherein the composition exhibits a release profile of the amine-containing compound comprising a substantial portion that is representative of zero-order release kinetics under in vitro conditions.

72. A sustained-release oral pharmaceutical composition comprising within a single dosage form:

a hydrophilic matrix comprising a hydroxypropyl methylcellulose;

a therapeutically effective amount of an amine-containing compound selected from the group consisting of ritodrine, a salt thereof, and combinations thereof; and a salt of a non-steroidal anti-inflammatory drug (NSAID) selected from the group consisting of a salt of naproxen, and combinations thereof;

wherein the amine-containing compound and the salt of an NSAID are within the hydrophilic matrix; and wherein the composition exhibits a release profile of the amine-containing compound comprising a substantial portion that is representative of zero-order release kinetics under in vitro conditions.

73. A sustained-release oral pharmaceutical composition comprising within a single dosage form:

a hydrophilic matrix comprising a hydroxypropyl methylcellulose;

24 a therapeutically effective amount of an amine-containing compound selected from the group consisting of memantine, a salt thereof, and combinations thereof; and a salt of a non-steroidal anti-inflammatory drug (NSAID) selected from the group consisting of a salt of naproxen, and combinations thereof;

wherein the amine-containing compound and the salt of an NSAID are within the hydrophilic matrix; and wherein the composition exhibits a release profile of the amine-containing compound comprising a substantial portion that is representative of zero-order release kinetics under in vitro conditions.

74. A sustained-release oral pharmaceutical composition comprising within a single dosage form:

a hydrophilic matrix comprising a hydroxypropyl methylcellulose;

a therapeutically effective amount of an amine-containing compound selected from the group consisting of amantadine, a salt thereof, and combinations thereof; and a salt of a non-steroidal anti-inflammatory drug (NSAID) selected from the group consisting of a salt of naproxen, and combinations thereof;

wherein the amine-containing compound and the salt of an NSAID are within the hydrophilic matrix; and wherein the composition exhibits a release profile of the amine-containing compound comprising a substantial portion that is representative of zero-order release kinetics under in vitro conditions.

75. A sustained-release oral pharmaceutical composition comprising within a single dosage form:

a hydrophilic matrix;

a therapeutically effective amount of an amine-containing compound selected from the group consisting of dextromethorphan, cyclobenzaprine, benztropine, ritodrine, mamantine, amantadine, salts thereof, and combinations thereof;

a salt of a non-steroidal anti-inflammatory drug (NSAID) selected from the group consisting of a salt of naproxen, diclofenac, ibuprofen, and combinations thereof; and a pharmaceutically acceptable anionic surfactant selected from the group consisting of sodium lauryl sulfate, docusate sodium, docusate calcium, and combinations thereof;

wherein the amine-containing compound the salt of an NSAID, and the anionic surfactant are within the hydrophilic matrix.

76. The composition of embodiment 75 which exhibits a release profile of the amine-containing compound comprising a substantial portion that is representative of zero-order release kinetics under in vitro conditions.

77. The composition of embodiment 75 or embodiment 76 wherein the amine-containing compound is selected from the group consisting of dextromethorphan, a salt thereof, and combinations thereof 78. The composition of embodiment 77 wherein the amine-containing compound comprises dextromethorphan hydrobromide.

79. The composition of embodiment 75 or embodiment 76 wherein the amine-containing compound is selected from the group consisting of cyclobenzaprine, a salt thereof, and combinations thereof 80. The composition of embodiment 79 wherein the amine-containing compound comprises cyclobenzaprine hydrochloride.

81. The composition of embodiment 75 or embodiment 76 wherein the amine-containing compound is selected from the group consisting of benztropine, a salt thereof, and combinations thereof 82. The composition of embodiment 81 wherein the amine-containing compound comprises benztropine mesylate.

83. The composition of embodiment 75 or embodiment 76 wherein the amine-containing compound is selected from the group consisting of ritodrine, a salt thereof, and combinations thereof 84. The composition of embodiment 83 wherein the amine-containing compound comprises ritodrine hydrochloride.

85. The composition of embodiment 75 or embodiment 76 wherein the amine-containing compound is selected from the group consisting of memantine, a salt thereof, and combinations thereof 86. The composition of embodiment 85 wherein the amine-containing compound comprises memantine hydrochloride.

87. The composition of embodiment 75 or embodiment 76 wherein the amine-containing compound is selected from the group consisting of amantadine, a salt thereof, and combinations thereof 88. The composition of embodiment 87 wherein the amine-containing compound comprises amantadine hydrochloride.

89. The composition of any one of embodiments 75 through 88 wherein the pharmaceutically acceptable anionic surfactant is docusate sodium.

90. The composition of any one of embodiments 75 through 89 wherein the hydrophilic polymeric compound comprises a cellulose ether.

91. The composition of embodiment 90 wherein the cellulose ether comprises a hydroxyalkyl cellulose, a carboxyalkyl cellulose, and combinations thereof 92. The composition of embodiment 90 wherein the cellulose ether comprises a methylcellulose, a hydroxypropyl methylcellulose, and combinations thereof 93. The composition of embodiment 90 wherein the cellulose ether comprises a hydroxypropyl methylcellulose.

94. A sustained-release oral pharmaceutical composition comprising within a single dosage form:
a hydrophilic matrix comprising a hydroxypropyl methylcellulose;
a therapeutically effective amount of an amine-containing compound selected from the group consisting of dextromethorphan, a salt thereof, and combinations thereof;
a salt of a non-steroidal anti-inflammatory drug (NSAID) selected from the group consisting of a salt of naproxen, and combinations thereof; and
a pharmaceutically acceptable anionic surfactant selected from the group consisting of docusate sodium, docusate calcium, and combinations thereof;
wherein the amine-containing compound, the salt of an NSAID, and the anionic surfactant are within the hydrophilic matrix.

95. A sustained-release oral pharmaceutical composition comprising within a single dosage form:
a hydrophilic matrix comprising a hydroxypropyl methylcellulose;
a therapeutically effective amount of an amine-containing compound selected from the group consisting of cyclobenzaprine, a salt thereof, and combinations thereof;
a salt of a non-steroidal anti-inflammatory drug (NSAID) selected from the group consisting of a salt of naproxen, and combinations thereof; and
a pharmaceutically acceptable anionic surfactant selected from the group consisting of docusate sodium, docusate calcium, and combinations thereof;
wherein the amine-containing compound, the salt of an NSAID, and the anionic surfactant are within the hydrophilic matrix.

96. A sustained-release oral pharmaceutical composition comprising within a single dosage form:
a hydrophilic matrix comprising a hydroxypropyl methylcellulose;
a therapeutically effective amount of an amine-containing compound selected from the group consisting of benztropine, a salt thereof, and combinations thereof;
a salt of a non-steroidal anti-inflammatory drug (NSAID) selected from the group consisting of a salt of naproxen, and combinations thereof; and
a pharmaceutically acceptable anionic surfactant selected from the group consisting of docusate sodium, docusate calcium, and combinations thereof;
wherein the amine-containing compound, the salt of an NSAID, and the anionic surfactant are within the hydrophilic matrix.

97. A sustained-release oral pharmaceutical composition comprising within a single dosage form:
a hydrophilic matrix comprising a hydroxypropyl methylcellulose;
a therapeutically effective amount of an amine-containing compound selected from the group consisting of ritodrine, a salt thereof, and combinations thereof;
a salt of a non-steroidal anti-inflammatory drug (NSAID) selected from the group consisting of a salt of naproxen, and combinations thereof; and
a pharmaceutically acceptable anionic surfactant selected from the group consisting of docusate sodium, docusate calcium, and combinations thereof;
wherein the amine-containing compound, the salt of an NSAID, and the anionic surfactant are within the hydrophilic matrix.

98. A sustained-release oral pharmaceutical composition comprising within a single dosage form:
a hydrophilic matrix comprising a hydroxypropyl methylcellulose;
a therapeutically effective amount of an amine-containing compound selected from the group consisting of memantine, a salt thereof, and combinations thereof;
a salt of a non-steroidal anti-inflammatory drug (NSAID) selected from the group consisting of a salt of naproxen, and combinations thereof; and
a pharmaceutically acceptable anionic surfactant selected from the group consisting of docusate sodium, docusate calcium, and combinations thereof;
wherein the amine-containing compound, the salt of an NSAID, and the anionic surfactant are within the hydrophilic matrix.

99. A sustained-release oral pharmaceutical composition comprising within a single dosage form:
a hydrophilic matrix comprising a hydroxypropyl methylcellulose;
a therapeutically effective amount of an amine-containing compound selected from the group consisting of amantadine, a salt thereof, and combinations thereof;
a salt of a non-steroidal anti-inflammatory drug (NSAID) selected from the group consisting of a salt of naproxen, and combinations thereof; and a pharmaceutically acceptable anionic surfactant selected from the group consisting of docusate sodium, docusate calcium, and combinations thereof;

wherein the amine-containing compound, the salt of an NSAID, and the anionic surfactant are within the hydrophilic matrix.

100. The composition of any one of embodiments 94 through 99 which exhibits a release profile of the amine-containing compound comprising a substantial portion that is representative of zero-order release kinetics under in vitro conditions.

101. A method of providing a desired effect in a subject, the method comprising administering to a subject a composition of any one of embodiments 1 through 100.

102. The method of embodiment 101 wherein administering the composition comprises administering once or twice per day.

103. The method of embodiment 102 wherein administering the composition comprises administering once per day.

EXAMPLES

Objects and advantages of this invention are further illustrated by the following examples, but the particular materials and amounts thereof recited in these examples, as well as other conditions and details, should not be construed to unduly limit this invention.

Sources for materials used in the following Examples are as follows:

| Component | Vendor |
| --- | --- |
| Dextromethorphan Hydrobromide | Wockhardt Limited |
| Methocel K4M | Dow Chemical |
| Avicel PH-302 | FMC Biopolymer |
| Naproxen Sodium | Albemarle Corp. |
| Naproxen | Sigma-Aldrich, Inc. |
| Ibuprofen Sodium | Sigma-Aldrich, Inc. |
| Ibuprofen | Sigma-Aldrich, Inc. |
| Docusate Sodium | Cytec Industries, Inc. |
| Benztropine Mesylate | Spectrum Chemical |
| Sodium Lauryl Sulfate | Fisher Scientific |
| Ritodrine HCl | Sigma-Aldrich |

Example 1

Preparation of Sustained-Release Hydrophilic Matrix Tablets Containing Dextromethorphan Hydrobromide (DXM), Naproxen Sodium (NAP), and Docusate Sodium (DSS) at Benchtop Scale Each hydrophilic matrix tablet lot was produced by dry-blending the active substance(s) and excipients together followed by direct compression. The DXM and NAP (when present) were added together with all excipients in an HDPE bag. Blending was accomplished by manually mixing the contents of the bag for five minutes. Aliquots of the blend were massed out using an analytical balance and were compressed using a Manesty DC16 press. Each tablet aliquot was added to the die manually and compressed at a speed of 5 rpm. Lots without NAP were compressed using 0.3125-inch round, concave Natoli tooling (HOB No. 91300), while lots containing NAP were compressed using 0.3750-inch round, concave Natoli tooling (HOB No. 91380). The compression force was varied until a tablet breaking force of 14-16 kPa was consistently achieved.

TABLE 1

Prototype formulation compositions (mg/tablet)

| Lot No. | Dextromethorphan Hydrobromide | Methocel K4M | Avicel PH-302 | Naproxen Sodium | Granular Docusate Sodium | Total Tablet Mass (mg) |
| --- | --- | --- | --- | --- | --- | --- |
| Prototype 1-1 | 15.0 | 120.0 | 45.0 | | | 180.0 |
| Prototype 1-2 | 15.0 | 120.0 | 45.0 | | 17.6 | 197.6 |
| Prototype 1-3 | 15.0 | 120.0 | 45.0 | | 117.7 | 297.7 |
| Prototype 1-4 | 15.0 | 120.0 | 45.0 | 220.0 | | 400.0 |
| Prototype 1-5 | 15.0 | 120.0 | 45.0 | 220.0 | 8.8 | 408.8 |
| Prototype 1-6 | 15.0 | 120.0 | 45.0 | 220.0 | 17.6 | 417.6 |
| Prototype 1-7 | 15.0 | 120.0 | 45.0 | 220.0 | 29.4 | 429.4 |
| Prototype 1-8 | 15.0 | 120.0 | 45.0 | 220.0 | 117.7 | 517.7 |

USP Apparatus 2 was used for the dissolution testing of the prototype tablets produced. The dissolution samples were assayed for DXM using HPLC with UV detection at 280 nm. The system parameters for both the chromatographic and dissolution analysis are shown below.

System: Hewlett Packard 1100 Series HPLC System

Column: Phenomenex Jupiter C18, 250×4 6 mm ID, 5μ, 300 Å Part No.: 00G-4053-EO

Detector: UV detector, 280 nm

Mobile Phase A: 94.7/5.0/0.3 (v/v/v) water/methanol/TFA

Mobile Phase B: Pure methanol

Method Type: Gradient

Flow Rate: 1.5 mL/min

Injection Volume: 30 μL

Run Time: 8.00 minutes (8.01-10.00 minutes is reequilibration)

Peakwidth: >0.1 min

Column Temperature: 35° C.

Autosampler temp: Ambient

TABLE 2

Gradient profile for HPLC mobile phases A and B

| Initial | 60% A | 40% B |
|---|---|---|
| 8.00 | 10% A | 90% B |
| 8.01 | 60% A | 40% B |
| 10.00 | 60% A | 40% B |

TABLE 3

Dissolution parameters

| Parameters | Requirements |
|---|---|
| Method Type | USP Apparatus 2 (Paddle Method) |
| Rotation Speed | 50 rpm |
| Dissolution Media | pH 7.5 phosphate buffer (0.05M, potassium phosphate monobasic 0.68%/NaOH 0.164%) |
| Media Volume | 900 mL |
| Media Temperature | 37.0 ± 0.5° C. |
| Sampling Time Points | 1, 2, 4, 6, 8, 10 and 12 hours |
| | 1, 2, 3, 6, 9, and 12 hours |
| Sampling Volume | 10 mL without media replacement (Use 10 μm Full-Flow Filter) | addition of the NSAID salt to the matrix increases the rate and extent of DXM release, while also causing the release rate to become constant.

Example 2

Preparation of Sustained-Release Hydrophilic Matrix Tablets Containing Dextromethorphan Hydrobromide (DXM), Naproxen, Naproxen Sodium, Ibuprofen, Ibuprofen Sodium, and Docusate Sodium (DSS) at Benchtop Scale Each hydrophilic matrix tablet lot was produced by dry-blending the active substance(s) and excipients together followed by direct compression. The DXM and NSAID/NSAID salt were added together with all excipients in an HDPE bag. Blending was accomplished by manually mixing the contents of the bag for five minutes. Aliquots of the blend were massed out using an analytical balance and were compressed using a Manesty DC16 press. Each tablet aliquot was added to the die manually and compressed at a speed of 5 rpm. All lots were compressed using 0.3750-inch round, concave Natoli tooling (HOB No. 91380). The compression force was varied until a tablet breaking force of 14-16 kPa was consistently achieved.

TABLE 4

Prototype formulation compositions (mg/tablet)

Formulation (mg/tablet)

| Lot No. | DXM | Methocel K4M | Avicel PH-302 | Naproxen Sodium | Naproxen | Ibuprofen Sodium | Ibuprofen | Granular Docusate Sodium | Total Tablet Mass (mg) |
|---|---|---|---|---|---|---|---|---|---|
| 2-1 | 15.0 | 120.0 | 45.0 | 220.0 | | | | 17.6 | 417.6 |
| 2-2 | 15.0 | 120.0 | 45.0 | | 220.0 | | | 17.6 | 417.6 |
| 2-3 | 15.0 | 120.0 | 45.0 | | | 220.0 | | 17.6 | 417.6 |
| 2-4 | 15.0 | 120.0 | 45.0 | | | | 220.0 | 17.6 | 417.6 |

FIG. 1 illustrates zero-order release kinetics over 12 hours for DXM from the hydrophilic matrix containing naproxen sodium both with and without docusate sodium. Prototype 1-4 contains no DSS, indicating that the surfactant is not critical to achieving linear (i.e., zero-order) release kinetics. Prototypes 1-5 through 1-8 reveal that the addition of surfactant into the hydrophilic matrix does impact the rate and extent of release, with higher DSS levels showing a slower release rate and a lower extent of release at 12 hours. Regardless of DSS level, all dissolution profiles in the presence of naproxen sodium are zero-order.

To further illustrate the importance of naproxen sodium and DSS to the release kinetics of DXM from the hydrophilic matrix, FIG. 2 shows dissolution profiles for several formulations in which key components have been added or removed. Prototype 1-1 shows the release of DXM from the hydrophilic matrix in the absence of naproxen sodium and DSS. This formulation shows the largest extent of release; however, the release profile is non-linear, indicating that zero-order release is not achieved. Prototypes 1-2 and 1-3 show the DXM release profile at increasing levels of DSS (15 mg and 100 mg, respectively), revealing that surfactant level can also be used to control the rate and extent of DXM release when the NSAID salt is absent from the hydrophilic matrix. Prototypes 1-6 and 1-8 show DXM release profiles at the same two DSS concentrations (15 mg and 100 mg, respectively) in the presence of naproxen sodium. Here, the USP Apparatus 2 was used for the dissolution testing of the prototype tablets produced. The dissolution samples were assayed for DXM using HPLC with UV detection at 280 nm. The system parameters for both the chromatographic and dissolution analysis are shown below.

System: Hewlett Packard 1100 Series HPLC System
Column: Phenomenex Jupiter C18, 250×4 6 mm ID, 5μ, 300 Å Part No.: 00G-4053-EO
Detector: UV detector, 280 nm
Mobile Phase A: 94.7/5.0/0.3 (v/v/v) water/methanol/TFA
Mobile Phase B: Pure methanol
Method Type: Gradient
Flow Rate: 1.5 mL/min
Injection Volume: 30 μL
Run Time: 8.00 minutes (8.01-10.00 minutes is reequilibration)
Peakwidth: >0.1 min
Column Temperature: 35° C.
Autosampler temp: Ambient

TABLE 5

Gradient profile for HPLC mobile phases A and B

| Initial | 60% A | 40% B |
|---|---|---|
| 8.00 | 10% A | 90% B |
| 8.01 | 60% A | 40% B |
| 10.00 | 60% A | 40% B |

TABLE 6

Dissolution parameters

| Parameters | Requirements |
| --- | --- |
| Method Type | USP Apparatus 2 (Paddle Method) |
| Rotation Speed | 50 rpm |

TABLE 6-continued

Dissolution parameters

| Parameters | Requirements |
| --- | --- |
| Dissolution Media | pH 7.5 phosphate buffer (0.05M, potassium phosphate monobasic 0.68%/NaOH 0.164%) |
| Media Volume | 900 mL |
| Media Temperature | 37.0 ± 0.5° C. |
| Sampling Time Points | 1, 2, 4, 6, 8, 10 and 12 hours |
| | 1, 2, 3, 6, 9, and 12 hours |
| Sampling Volume | 10 mL without media replacement (Use 10 µm Full-Flow Filter) |

FIG. 3 shows dissolution profiles for DXM from the hydrophilic matrix in presence of NSAID and NSAID salts, demonstrating that zero-order release kinetics depends on the presence of an NSAID salt form (as opposed to a neutral free molecule). Prototypes 2-1 and 2-3 contain sodium salts of naproxen and ibuprofen, respectively. Prototypes 2-2 and 2-4 contain the free base of naproxen and ibuprofen, respectively. All prototypes contain 15 mg of DSS. As shown in the figure, dissolution profiles for the two prototypes containing the NSAID salt forms are linear, indicating zero-order release for DXM from these formulations over 12 hours. Conversely, the two prototypes containing the NSAID free base forms show deviation from linearity, indicating that the release rate for DXM from these formulations is not constant. (Note: Linear fits to each curve have been included in the figure to guide the eye.)

Example 3

Preparation of Sustained-Release Hydrophilic Matrix Tablets Containing Cyclobenzaprine Hydrochloride (CBP), Naproxen Sodium (NAP), and Docusate Sodium (DSS) at Benchtop Scale Each hydrophilic matrix tablet lot was produced by dry-blending the active substance(s) and excipients together followed by direct compression. The CBP and NAP (when present) were added together with all excipients in an HDPE bag. Blending was accomplished by manually mixing the contents of the bag for five minutes. Aliquots of the blend were massed out using an analytical balance and were compressed using a Manesty DC16 press. Each tablet aliquot was added to the die manually and compressed at a speed of 5 rpm. Lots without NAP were compressed using 0.3125-inch round, concave Natoli tooling (HOB No. 91300), while lots containing NAP were compressed using 0.3750-inch round, concave Natoli tooling (HOB No. 91380). The compression force was varied until a tablet breaking force of 14-16 kPa was consistently achieved.

TABLE 7

Prototype formulation compositions (mg/tablet)

| Lot No. | Cyclobenzaprine Hydrochloride | Methocel K4M | Avicel PH-302 | Naproxen Sodium | Granular Docusate Sodium | Total Tablet Mass (mg) |
| --- | --- | --- | --- | --- | --- | --- |
| Prototype 3-1 | 15.0 | 120.0 | 45.0 | | | 180.0 |
| Prototype 3-2 | 15.0 | 120.0 | 45.0 | | 17.6 | 197.6 |
| Prototype 3-3 | 15.0 | 120.0 | 45.0 | | 117.7 | 297.7 |
| Prototype 3-4 | 15.0 | 120.0 | 45.0 | 220.0 | 17.6 | 417.6 |
| Prototype 3-5 | 15.0 | 120.0 | 45.0 | 220.0 | 117.7 | 517.7 |

USP Apparatus 2 was used for the dissolution testing of the prototype tablets produced. The dissolution samples were assayed for CBP using HPLC with UV detection at 280 nm. The system parameters for both the chromatographic and dissolution analysis are shown below.

System: Hewlett Packard 1100 Series HPLC System

Column: Phenomenex Jupiter C18, 250×4 6 mm ID, 5µ, 300 Å Part No.: 00G-4053-EO

Detector: UV detector, 280 nm

Mobile Phase A: 94.7/5.0/0.3 (v/v/v) water/methanol/TFA

Mobile Phase B: Pure methanol

Method Type: Gradient

Flow Rate: 1.5 mL/min

Injection Volume: 30 µL

Run Time: 8.00 minutes (8.01-10.00 minutes is reequilibration)

Peakwidth: >0.1 min

Column Temperature: 35° C.

Autosampler temp: Ambient

TABLE 8

Gradient profile for HPLC mobile phases A and B

| Initial | 60% A | 40% B |
| --- | --- | --- |
| 8.00 | 10% A | 90% B |
| 8.01 | 60% A | 40% B |
| 10.00 | 60% A | 40% B |

TABLE 9

Dissolution parameters

| Parameters | Requirements |
| --- | --- |
| Method Type | USP Apparatus 2 (Paddle Method) |
| Rotation Speed | 50 rpm |
| Dissolution Media | pH 7.5 phosphate buffer (0.05M, potassium phosphate monobasic 0.68%/NaOH 0.164%) |
| Media Volume | 900 mL |
| Media Temperature | 37.0 ± 0.5° C. |

TABLE 9-continued

| Dissolution parameters | |
| --- | --- |
| Parameters | Requirements |
| Sampling Time Points | 1, 2, 4, 6, 8, 10 and 12 hours |
|  | 1, 2, 3, 6, 9, and 12 hours |
| Sampling Volume | 10 mL without media replacement (Use 10 μm Full-Flow Filter) |

To illustrate the importance of naproxen sodium and DSS to the release kinetics of CBP from the hydrophilic matrix, FIG. 4 shows dissolution profiles for several formulations in which key components have been added or removed. Prototype 3-1 shows the release of CBP from the hydrophilic matrix in the absence of naproxen sodium and DSS. This formulation shows that the release profile is non-linear, indicating that zero-order release is not achieved. Prototypes 3-2 and 3-3 show the CBP release profile at increasing levels of DSS (15 mg and 100 mg, respectively), revealing that surfactant level can be used to control the rate and extent of CBP release when the NSAID salt is absent from the hydrophilic matrix. Prototypes 3-4 and 3-5 show CBP release profiles at the same two DSS concentrations (15 mg and 100 mg, respectively) in the presence of naproxen sodium. Here, the addition of the NSAID salt to the matrix increases the rate and extent of CBP release, while also causing the release rate to become constant (zero-order).

Example 4

Preparation of Sustained-Release Hydrophilic Matrix Tablets Containing Benztropine Mesylate (BTP), Naproxen Sodium (NAP), and Docusate Sodium (DSS) at Benchtop Scale Each hydrophilic matrix tablet lot was produced by dry-blending the active substance(s) and excipients together followed by direct compression. The BTP and NAP (when present) were added together with all excipients in an HDPE bag. Blending was accomplished by manually mixing the contents of the bag for five minutes. Aliquots of the blend were massed out using an analytical balance and were compressed using a Manesty DC16 press. Each tablet aliquot was added to the die manually and compressed at a speed of 5 rpm. Lots without NAP were compressed using 0.3125-inch round, concave Natoli tooling (HOB No. 91300), while lots containing NAP were compressed using 0.3750-inch round, concave Natoli tooling (HOB No. 91380). The compression force was varied until a tablet breaking force of 14-16 kPa was consistently achieved.

TABLE 10

Prototype formulation compositions (mg/tablet)

| Lot No. | Benztropine Mesylate | Methocel K4M | Avicel PH-302 | Naproxen Sodium | Granular Docusate Sodium | Total Tablet Mass (mg) |
| --- | --- | --- | --- | --- | --- | --- |
| Prototype 4-1 | 15.0 | 120.0 | 45.0 |  |  | 180.0 |
| Prototype 4-2 | 15.0 | 120.0 | 45.0 |  | 17.6 | 197.6 |
| Prototype 4-3 | 15.0 | 120.0 | 45.0 |  | 117.7 | 297.7 |
| Prototype 4-4 | 15.0 | 120.0 | 45.0 | 220.0 | 17.6 | 417.6 |
| Prototype 4-5 | 15.0 | 120.0 | 45.0 | 220.0 | 117.7 | 517.7 |

USP Apparatus 2 was used for the dissolution testing of the prototype tablets produced. The dissolution samples were assayed for BTP using HPLC with UV detection at 254 nm. The system parameters for both the chromatographic and dissolution analysis are shown below.

System: Hewlett Packard 1100 Series HPLC System
Column: Phenomenex Jupiter C18, 250×4.6 mm ID, 5μ, 300 Å Part No.: 00G-4053-EO
Detector: UV detector, 254 nm
Mobile Phase A: 94.7/5.0/0.3 (v/v/v) water/methanol/TFA
Mobile Phase B: Pure methanol
Method Type: Gradient
Flow Rate: 1.5 mL/min
Injection Volume: 30 μL
Run Time: 8.00 minutes (8.01-10.00 minutes is reequilibration)
Peakwidth: >0.1 min
Column Temperature: 35° C.
Autosampler temp: Ambient

TABLE 11

Gradient profile for HPLC mobile phases A and B

| Initial | 60% A | 40% B |
| --- | --- | --- |
| 8.00 | 10% A | 90% B |
| 8.01 | 60% A | 40% B |
| 10.00 | 60% A | 40% B |

TABLE 12

| Dissolution parameters | |
| --- | --- |
| Parameters | Requirements |
| Method Type | USP Apparatus 2 (Paddle Method) |
| Rotation Speed | 50 rpm |
| Dissolution Media | pH 7.5 phosphate buffer (0.05M, potassium phosphate monobasic 0.68%/NaOH 0.164%) |
| Media Volume | 900 mL |
| Media Temperature | 37.0 ± 0.5° C. |
| Sampling Time Points | 1, 2, 4, 6, 8, 10 and 12 hours |
|  | 1, 2, 3, 6, 9, and 12 hours |
| Sampling Volume | 10 mL without media replacement (Use 10 μm Full-Flow Filter) |

To illustrate the importance of naproxen sodium and DSS to the release kinetics of BTP from the hydrophilic matrix, FIG. 5 shows dissolution profiles for several formulations in which key components have been added or removed. Prototype 4-1 shows the release of BTP from the hydrophilic matrix in the absence of naproxen sodium and DSS. This formulation shows that the release profile is non-linear, indicating that zero-order release is not achieved. Prototypes 4-2 and 4-3 show the BTP release profile at increasing levels of DSS (15 mg and 100 mg, respectively), revealing that surfactant level can be used to control the rate and extent of BTP release when the NSAID salt is absent from the hydrophilic matrix. Prototypes 4-4 and 4-5 show BTP release profiles at the same two DSS concentrations (15 mg and 100 mg, respectively) in the presence of naproxen sodium. Here, the addition of the NSAID salt to the matrix increases the rate and extent of BTP release, while also causing the release rate to become constant (zero-order).

Example 5

Preparation of Sustained-Release Hydrophilic Matrix Tablets Containing Dextromethorphan Hydrobromide (DXM), Naproxen Sodium (NAP), and Sodium Lauryl Sulfate (SLS) at Benchtop Scale Each hydrophilic matrix tablet lot was produced by dry-blending the active substance(s) and excipients together followed by direct compression. The DXM and NAP (when present) were added together with all excipients in an HDPE bag. Blending was accomplished by manually mixing the contents of the bag for five minutes. Aliquots of the blend were massed out using an analytical balance and were compressed using a Manesty DC16 press. Each tablet aliquot was added to the die manually and compressed at a speed of 5 rpm. Lots without NAP were compressed using 0.3125-inch round, concave Natoli tooling (HOB No. 91300), while lots containing NAP were compressed using 0.3750-inch round, concave Natoli tooling (HOB No. 91380). The compression force was varied until a target tablet breaking force of 14-16 kPa was consistently achieved. For several of the prototype formulations, the target tablet breaking force of 15 kPa could not be achieved. In these cases, the compression force was increased until a maximum breaking force was realized: 8 kPa for Prototype 5-2, 9 kPa for Prototype 5-3, 14 kPa for Prototype 5-5, and 12 kPa for prototype 5-6.

TABLE 13

Prototype formulation compositions (mg/tablet)

| Lot No. | Dextromethorphan Hydrobromide | Methocel K4M | Avicel PH-302 | Naproxen Sodium | Sodium Lauryl Sulfate | Total Tablet Mass (mg) |
|---|---|---|---|---|---|---|
| Prototype 5-1 | 15.0 | 120.0 | 45.0 |  | 7.5 | 187.5 |
| Prototype 5-2 | 15.0 | 120.0 | 45.0 |  | 15.0 | 195.0 |
| Prototype 5-3 | 15.0 | 120.0 | 45.0 |  | 25.0 | 205.0 |
| Prototype 5-4 | 15.0 | 120.0 | 45.0 | 220.0 | 7.5 | 407.5 |
| Prototype 5-5 | 15.0 | 120.0 | 45.0 | 220.0 | 15.0 | 415.0 |
| Prototype 5-6 | 15.0 | 120.0 | 45.0 | 220.0 | 25.0 | 425.0 |

USP Apparatus 2 was used for the dissolution testing of the prototype tablets produced. The dissolution samples were assayed for DXM using HPLC with UV detection at 280 nm. The system parameters for both the chromatographic and dissolution analysis are shown below.
System: Agilent 1100 Series HPLC System
Column: Phenomenex Jupiter C18, 250×4 6 mm ID, 5μ, 300 ÅPart No.: 00G-4053-EO
Detector: UV detector, 280 nm
Mobile Phase A: 94.7/5.0/0.3 (v/v/v) water/methanol/TFA
Mobile Phase B: Pure methanol
Method Type: Gradient
Flow Rate: 1.5 mL/min
Injection Volume: 30 μL
Run Time: 8.00 minutes (8.01-10.00 minutes is reequilibration)
Peakwidth: >0.1 min
Column Temperature: 35° C.
Autosampler temp: Ambient

TABLE 14

Gradient profile for HPLC mobile phases A and B

| | | |
|---|---|---|
| Initial | 60% A | 40% B |
| 8.00 | 10% A | 90% B |
| 8.01 | 60% A | 40% B |
| 10.00 | 60% A | 40% B |

TABLE 15

Dissolution parameters

| Parameters | Requirements |
|---|---|
| Method Type | USP Apparatus 2 (Paddle Method) |
| Rotation Speed | 50 rpm |
| Dissolution Media | pH 7.5 phosphate buffer (0.05M, potassium phosphate monobasic 0.68%/NaOH 0.164%) |
| Media Volume | 900 mL |
| Media Temperature | 37.0 ± 0.5 C. |
| Sampling Time Points | 1, 3, 6, 9, and 12 hours |
| Sampling Volume | 10 mL without media replacement (Use 10 μm Full-Flow Filter) |

FIG. 6 illustrates first-order release kinetics over 12 hours for DXM formulations that contain varying levels of SLS (7.5 mg-25 mg) without the addition of naproxen sodium. The results are similar to those seen for comparable prototypes that contain DXM, DSS and no naproxen sodium (FIG. 2). The surfactant (DSS or SLS) strongly retards the release of DXM. Close inspection of the data reveals first-order release, even for the slower releasing formulations.

Addition of naproxen sodium to the formulations containing SLS results in zero-order drug release profiles (FIG. 7). Again, this is similar to release profiles seen for formulations containing DSS. Comparison to matrix tablets of similar composition (FIG. 6) shows that the addition of naproxen sodium increases the rate and linearizes the release profiles. For tablets containing DXM, SLS and naproxen sodium, release profiles are very similar for increasing levels of SLS with the highest SLS level releasing slightly faster than the other two. It should be noted that other formulation parameters (for example grade of HPMC) could be used to further tailor release profiles for formulations containing surfactant.

Example 6

Preparation of Sustained-Release Hydrophilic Matrix Tablets Containing Dextromethorphan Hydrobromide (DXM), Docusate Sodium (DSS) and Varying Levels of Naproxen Sodium (NAP) at Benchtop Scale Each hydrophilic matrix tablet lot was produced by dry-blending the active substance(s) and excipients together followed by direct compression. The DXM and NAP were added together with all excipients in an HDPE bag. Blending was accomplished by manually mixing the contents of the bag for five minutes. Aliquots of the blend were massed out using an analytical balance and were compressed using a Manesty DC16 press. Each tablet aliquot was added to the die manually and compressed at a speed of 5 rpm. Prototypes 6-1, 6-2 and 6-3 were compressed using 0.3125-inch round, concave Natoli tooling (HOB No. 91300), while prototype 6-4 was compressed using 0.3750-inch round, concave Natoli tooling (HOB No. 91380). The compression force was varied until a tablet breaking force of 14-16 kPa was consistently achieved.

TABLE 16

Prototype formulation compositions (mg/tablet)

| Lot No. | Formulation (mg/tablet) | | | | | |
|---|---|---|---|---|---|---|
| | Dextromethorphan Hydrobromide | Methocel K4M | Avicel PH-302 | Naproxen Sodium | Granular Docusate Sodium | Total Tablet Mass (mg) |
| Prototype 6-1 | 15.0 | 120.0 | 45.0 | 27.5 | 17.6 | 225.1 |
| Prototype 6-2 | 15.0 | 120.0 | 45.0 | 55.0 | 17.6 | 252.6 |
| Prototype 6-3 | 15.0 | 120.0 | 45.0 | 110.0 | 17.6 | 307.6 |
| Prototype 6-4 | 15.0 | 120.0 | 45.0 | 220.0 | 17.6 | 417.6 |

USP Apparatus 2 was used for the dissolution testing of the prototype tablets produced. The dissolution samples were assayed for DXM using HPLC with UV detection at 280 nm. The system parameters for both the chromatographic and dissolution analysis are shown below.
System: Agilent 1100 Series HPLC System
Column: Phenomenex Jupiter C18, 250×4 6 mm ID, 5μ, 300 Å Part No.: 00G-4053-EO
Detector: UV detector, 280 nm
Mobile Phase A: 94.7/5.0/0.3 (v/v/v) water/methanol/TFA
Mobile Phase B: Pure methanol
Method Type: Gradient
Flow Rate: 1.5 mL/min
Injection Volume: 30 μL
Run Time: 8.00 minutes (8.01-10.00 minutes is reequilibration)
Peakwidth: >0.1 min
Column Temperature: 35° C.
Autosampler temp: Ambient

TABLE 17

Gradient profile for HPLC mobile phases A and B

| Initial | 60% A | 40% B |
|---|---|---|
| 8.00 | 10% A | 90% B |

TABLE 17-continued

Gradient profile for HPLC mobile phases A and B

| 8.01 | 60% A | 40% B |
|---|---|---|
| 10.00 | 60% A | 40% B |

TABLE 18

Dissolution parameters

| Parameters | Requirements |
|---|---|
| Method Type | USP Apparatus 2 (Paddle Method) |
| Rotation Speed | 50 rpm |
| Dissolution Media | pH 7.5 phosphate buffer (0.05M, potassium phosphate monobasic 0.68%/NaOH 0.164%) |
| Media Volume | 900 mL |
| Media Temperature | 37.0 ± 0.5 C. |
| Sampling Time Points | 1, 3, 6, 9 and 12 hours |
| Sampling Volume | 10 mL without media replacement (Use 10 μm Full-Flow Filter) |

The impact of NSAID level on release profiles is shown in FIG. 8 for formulations having constant DXM and DSS with varying amounts of naproxen sodium. Zero-order release profiles are realized for naproxen sodium levels of 220 and 110 mg; however, slight deviation from zero-order can be seen for lower levels of naproxen sodium (55 and 27.5 mg), suggesting that there is a minimum threshold for naproxen sodium level needed to achieve constant release kinetics in the current formulation. Increasing naproxen sodium clearly has a significant impact on the rate of release, with the rate of DXM increasing with increasing NAP level.

Example 7

Evaluation of "Dose Dumping" and Drug Extraction for Prototype Formulations Containing Dextromethorphan Hydrobromide (DXM), Naproxen Sodium (NAP) and Docusate Sodium (DSS)

Each hydrophilic matrix tablet lot was produced by dry-blending the active substance(s) and excipients together followed by direct compression. The DXM and NAP were added together with all excipients in an HDPE bag. Blending was accomplished by manually mixing the contents of the bag for five minutes. Aliquots of the blend were massed out using an analytical balance and were compressed using a Manesty DC16 press. Each tablet aliquot was added to the die manually and compressed at a speed of 5 rpm. Prototypes 7-1, 7-2 and 7-3 were compressed using 0.3750-inch round, concave Natoli tooling (HOB No. 91380). The compression force was varied until a tablet breaking force of 14-16 kPa was consistently achieved.

TABLE 19

Prototype formulation compositions (mg/tablet)

| Lot No. | Dextromethorphan Hydrobromide | Methocel K4M | Avicel PH-302 | Naproxen Sodium | Granular Docusate Sodium | Total Tablet Mass (mg) |
|---|---|---|---|---|---|---|
| Prototype 7-1 | 15.0 | 120.0 | 45.0 | 220.0 | 17.6 | 417.6 |
| Prototype 7-2 | 15.0 | 120.0 | 45.0 | 220.0 | 29.4 | 429.4 |
| Prototype 7-3 | 15.0 | 120.0 | 45.0 | 220.0 | 58.8 | 458.8 |

Dose-Dumping

The hydroalcoholic "dose dumping" experiment investigates the in vitro drug release behavior in the presence of alcohol. The experiment models ingestion of a tablet with the concomitant use of alcoholic beverages (i.e., ethanol). In order to assess the potential for "dose dumping," the dissolution method was modified by changing the media to 0.1N HCl with varying levels of alcohol (ethanol). USP Apparatus 2 was used for the dissolution testing of the prototype tablets produced. The dissolution samples were assayed for DXM using HPLC with UV detection at 280 nm. The system parameters for both the chromatographic and dissolution analysis are shown below.

System: Agilent 1100 series HPLC system
Column: Phenomenex Jupiter C18, 250×4 6 mm ID, 5μ, 300 Å Part No.: 00G-4053-EO
Detector: UV detector, 280 nm
Mobile Phase A: 94.7/5.0/0.3 (v/v/v) water/methanol/TFA
Mobile Phase B: Pure methanol
Method Type: Gradient
Flow Rate: 1.5 mL/min
Injection Volume: 30 μL
Run Time: 8.00 minutes (8.01-10.00 minutes is reequilibration)
Peakwidth: >0.1 min
Column Temperature: 35° C.
Autosampler temp: Ambient

TABLE 20

Gradient profile for HPLC mobile phases A and B

| Initial | 60% A | 40% B |
|---|---|---|
| 8.00 | 10% A | 90% B |
| 8.01 | 60% A | 40% B |
| 10.00 | 60% A | 40% B |

TABLE 21

Dissolution parameters

| Parameters | Requirements |
|---|---|
| Method Type | USP Apparatus 2 (Paddle Method) |
| Rotation Speed | 50 rpm |
| Dissolution Media | pH 1.2 USP buffer pH 1.2 USP buffer (5% ethanol) pH 1.2 USP buffer (20% ethanol) |
| Media Volume | 900 mL |
| Media Temperature | 37.0 ± 0.5 C. |
| Sampling Time Points | 1, 3, 6, 9 and 12 hours |
| Sampling Volume | 8 mL without media replacement (Use 10 μm Full-Flow Filter) |

The purpose of this investigation was to measure the integrity of the dosage formulation using acidic, hydroalcoholic dissolution media. For this experiment, intact tablets were evaluated. Prototype 7-1 was evaluated since this formulation is expected to show significantly greater DXM release over 12 hours compared to Prototypes 7-2 and 7-3 based on evaluation of previous formulations of similar composition.

The experimental design was to simulate simultaneous oral ingestion of alcohol and the matrix tablet. Dissolution profiles are provided in FIG. 9. The results demonstrate that "dose dumping" does not occur, even with a 20% ethanol level in the dissolution media. In addition, zero-order release is maintained from 0-20% ethanol.

Drug Extraction

The small-volume extraction experiment models the attempted extraction of drug that a substance abuser might undertake. In this experiment, tablets were crushed and extracted with two common solvents, water and 40% alcohol. A single tablet was crushed and stirred with a small volume of solvent (50 mL). At time points of 30 minutes and 12 hours, aliquots were removed and assayed for both DXM and docusate. Prior to HPLC analysis the aliquots were filtered using a 10 μm full-flow filter and subsequently centrifuged at 1000 rpm for 30 minutes. The supernatant from this procedure was filled directly into HPLC vials for analysis. The HPLC assay for DXM has been described previously. The following HPLC method was developed to assay docusate:

System: Agilent 1100 series HPLC system
Column: YMC-Pack CN, 250 mm×4.6 mm ID, 5 μm, 120 Å Part number: CN12S052546WT
Detector: UV detector, 225 nm
Mobile Phase A: 0.02M tetrabutylammonium hydrogen sulfate
Mobile Phase B: Pure acetonitrile
Method Type: Isocratic 40% A/60% B
Flow Rate: 1.5 mL/min
Injection Volume: 10 μL
Run Time: 5 minutes
Peakwidth: >0.1 min
Column Temperature: 45° C.
Autosampler temp: Ambient

TABLE 22

Simultaneous Release of Dextromethorphan Hydrobromide and Docusate Sodium From Crushed Tablets to Assess Abuse Potential

| Formulation | Extraction Solvent | DXM Released in 30 minutes | Docusate Released in 30 minutes | DXM Released in 12 hours | Docusate Released in 12 hours |
|---|---|---|---|---|---|
| Prototype 1 | Water | 58% | 80% | 47% | 61% |
| Prototype 1 | Alcohol 40% | 93% | 91% | 100% | 98% |

TABLE 22-continued

Simultaneous Release of Dextromethorphan Hydrobromide
and Docusate Sodium From Crushed Tablets to Assess
Abuse Potential

| Formulation | Extraction Solvent | DXM Released in 30 minutes | Docusate Released in 30 minutes | DXM Released in 12 hours | Docusate Released in 12 hours |
|---|---|---|---|---|---|
| Prototype 2 | Water | 35% | 47% | 35% | 47% |
| Prototype 2 | Alcohol 40% | 95% | 93% | 114% | 108% |
| Prototype 3 | Water | 52% | 48% | 50% | 43% |
| Prototype 3 | Alcohol 40% | 68% | 67% | 102% | 95% |

The data (Table 22) demonstrates the simultaneous release of DXM and docusate from formulations containing different levels of docusate (Table 19). This data shows that extraction and separation of DXM and docusate from these formulations would require advanced chemical knowledge and substantial effort, and would likely be time-consuming. The commingling of DXM (or other active) and docusate would make injection of extracted solutions unattractive to an abuser and potentially harmful. Additionally, drying the solution to create a solid would be of no benefit to a drug abuser, as the solid would be impure and contain irritating docusate.

Example 8

Preparation of Sustained Release Hydrophilic Matrix Tablets Containing Amantadine Hydrochloride, Docusate Sodium (DSS) and Naproxen Sodium (NAP) at Benchtop Scale Each hydrophilic matrix tablet lot was produced by dry-blending the active substance(s) and excipients together followed by direct compression. The Amantadine HCl and NAP were added together with all excipients in an HDPE bag. Blending was accomplished by manually mixing the contents of the bag for five minutes. Aliquots of the blend were massed out using an analytical balance and were compressed using a Manesty DC16 press. Each tablet aliquot was added to the die manually and compressed at a speed of 10 rpm. Prototype 8-1 was compressed using 0.375 inch round, concave Natoli tooling (HOB No. 91380). Prototypes 8-2 and 8-3 were compressed using 0.3125 inch round, concave Natoli tooling (HOB #91300). The compression force was varied until a tablet breaking force of 14-16 kp was consistently achieved.

TABLE 23

Prototype formulation compositions (mg/tablet)

| Lot No. | Amantadine Hydrochloride | Methocel K4M | Avicel PH-302 | Naproxen Sodium | Granular Docusate Sodium | Total Tablet Mass (mg) |
|---|---|---|---|---|---|---|
| Prototype 8-1 | 15.0 | 120.1 | 45.0 | 219.8 | 17.1 | 417.0 |
| Prototype 8-2 | 15.0 | 120.1 | 45.0 | 0.0 | 17.1 | 197.2 |
| Prototype 8-3 | 15.0 | 120.1 | 45.0 | 0.0 | 0.0 | 180.1 |

Amantadine hydrochloride is a freely soluble drug that lacks a chromophore. Direct injection GC (gas chromatography) with a memantine internal standard allows for rapid and accurate analysis of dissolution samples. Baseline resolution between the amantadine and memantine internal standard ensures the integrity of the GC procedure.

Dissolution testing of matrix tablets was performed using USP Apparatus 2. At each specified time point, approximately 8 ml of media was removed using a stainless steel cannula. Samples were filtered using porous (full-flow) filters (QLA, Inc., Bridgewater, N.J., part number FIL035-01). A memantine internal standard was prepared by dissolving a known quantity of memantine standard in methanol and diluting (using volumetric glassware) to achieve a final concentration of ≈0.02 mg/ml. Each dissolution sample was diluted with an equal volume of memantine internal standard solution to result in a memantine internal standard concentration of ≈0.01 mg/ml. A chromatographic standard was prepared with the final concentration of amantadine at ≈0.01 mg/ml and memantine at ≈0.01 mg/ml. The final composition of samples and standards was 50%/50% (methanol/aqueous) on a volume/volume basis using this procedure. Every six samples were bracketed by chromatographic standards. Calculations were done using peak area ratios (amantadine area/memantine internal standard area). Drug released at each time point includes corrections for changes in vessel volume and the amount of drug removed during previous sample pulls. Media replacement was not performed. The system parameters for both the chromatographic and dissolution analysis are shown below.

TABLE 24

Dissolution parameters

| Parameters | Requirements |
|---|---|
| Method Type | USP Apparatus 2 (Paddle Method) |
| Rotation Speed | 50 rpm |
| Dissolution Media | pH 7.5 phosphate buffer (0.05M, potassium phosphate monobasic 0.68%/NaOH 0.164%) |
| Media Volume | 900 mL |
| Media Temperature | 37.0 ± 0.5 C. |
| Sampling Time Points | 1, 3, 6, 9, 12, 18 and 24 hours |
| Sampling Volume | 8 mL without media replacement (Use 35 μm Full-Flow Filter) |

TABLE 25

GC parameters

| Parameters | Requirements |
|---|---|
| Method Type | Gas Chromatography (HP 5890 Series II) |
| GC Column | Zebron ZB-5, 30 m × 0.53 mm, 5 μm film thickness, Phenomenex cat # 7HK-G002-39 |

TABLE 25-continued

GC parameters

| Parameters | Requirements |
| --- | --- |
| Injection Volume | 1.0 µl |
| Injection Mode | Direct injection |
| Injector Liner | Cyclo-Uniliner Liner, Siltek Deactivated, 4 × 6.3 × 78.5 mm, Restek cat.# 20338-214.5 |
| Injector Temperature | 220° C. |
| Detector Temperature | 250° C. |
| Carrier Gas | Helium at 3.0 psi |
| Detector | Flame ionization detector |
| Detector Gas | Hydrogen/air mixture |
| Gradient program | Initial temperature: 140°, hold for 15 minutes, ramp at 20° C./min for 5 minutes, final temp 240° C., hold for 1 minute at 240° |

The results for the amantadine hydrochloride matrix tablet containing naproxen sodium and DSS (Prototype 8-1) shows zero-order release. This demonstrates the applicability of the invention to drugs containing the primary amine functional group. The formulation that does not contain naproxen sodium and DSS (prototype 8-3) exhibits first-order release. Formulation 8-2 contains DSS (with no naproxen sodium) and shows a slower release compared to 8-3, providing addition evidence that docusate retards drug release without achieving a zero-order release profile. Note that the formulation containing amantadine hydrochloride, naproxen sodium and DSS (Prototype 8-1) exhibits sustained, zero-order release out to 24 hours, demonstrating the utility of the invention for q.d. as well as b.i.d, dosing.

Example 9

Preparation of Sustained Release Hydrophilic Matrix Tablets Containing Memantine Hydrochloride, Docusate Sodium (DSS) and Naproxen Sodium (NAP) at Benchtop Scale Each hydrophilic matrix tablet lot was produced by dry-blending the active substance(s) and excipients together followed by direct compression. The Memantine HCl and NAP were added together with all excipients in a 100 cc glass jar. Blending was accomplished using a GlobePharma Miniblend Table-Top Blender (10 min. @ 28 rpm). Aliquots of the blend were massed out using an analytical balance and were compressed using a Manesty DC16 press. Each tablet aliquot was added to the die manually and compressed at a speed of 3 rpm. Prototype 9-1 was compressed using 0.3750 in. round, concave Natoli tooling (HOB #91380) while prototypes 9-2 and 9-3 were compressed using 0.3125 in. round, concave Natoli tooling (HOB #91300). The compression force was varied until a tablet breaking force of 14-16 kp was consistently achieved.

Memantine hydrochloride is structurally similar to amantadine and lacks a chromophore. Though less soluble than amantadine hydrochloride, memantine hydrochloride is soluble in water. Direct injection GC (gas chromatography) with an amantadine internal standard allows for rapid and accurate analysis of dissolution samples. Baseline resolution between the memantine and the amantadine internal standard ensures the integrity of the GC procedure.

Dissolution testing of matrix tablets was performed using USP Apparatus 2. At each specified time point, approximately 8 ml of media was removed using a stainless steel cannula. Samples were filtered using porous (full-flow) filters (QLA, Inc., Bridgewater, N.J., part number FIL035-01). The amantadine internal standard was prepared by dissolving a known quantity of amantadine standard in methanol and diluting (using volumetric glassware) to achieve a final concentration of 0.02 mg/ml. Each dissolution sample was diluted with an equal volume of amantadine internal standard solution to result in an amantadine internal standard concentration of 0.01 mg/ml. A chromatographic standard was prepared with the final concentration of memantine at 0.01 mg/ml and amantadine at 0.01 mg/ml. The final composition of samples and standards was 50%/50% (methanol/aqueous) on a volume/volume basis using this procedure. Every six samples were bracketed by chromatographic standards. Calculations were done using peak area ratios (memantine area/amantadine internal standard area). Drug released at each time point includes corrections for changes in vessel volume and the amount of drug removed during previous sample pulls. Dissolution media replacement was not performed. The system parameters for both the chromatographic and dissolution analysis are shown below.

TABLE 27

Dissolution parameters

| Parameters | Requirements |
| --- | --- |
| Method Type | USP Apparatus 2 (Paddle Method) |
| Rotation Speed | 50 rpm |
| Dissolution Media | pH 7.5 phosphate buffer (0.05M, potassium phosphate monobasic 0.68%/NaOH 0.164%) |
| Media Volume | 900 mL |
| Media Temperature | 37.0 ± 0.5 C. |
| Sampling Time Points | 1, 3, 6, 9, 12, 18 and 24 hours |
| Sampling Volume | 8 mL without media replacement (Use 35 µm Full-Flow Filter) |

TABLE 26

Prototype formulation compositions (mg/tablet)

| Lot No. | Memantine Hydrochloride | Methocel K4M | Avicel PH-302 | Naproxen Sodium | Granular Docusate Sodium | Total Tablet Mass (mg) |
| --- | --- | --- | --- | --- | --- | --- |
| Prototype 9-1 | 15.0 | 120.1 | 45.0 | 219.8 | 17.1 | 417.0 |
| Prototype 9-2 | 15.0 | 120.1 | 45.0 | 0.0 | 17.1 | 197.2 |
| Prototype 9-3 | 15.0 | 120.1 | 45.0 | 0.0 | 0.0 | 180.1 |

TABLE 28

GC parameters

| Parameters | Requirements |
|---|---|
| Method Type | Gas Chromatography (HP 5890 Series II) |
| GC Column | Zebron ZB-5, 30 m × 0.53 mm, 5 μm film thickness, Phenomenex cat # 7HK-G002-39 |

TABLE 28-continued

GC parameters

| Parameters | Requirements |
|---|---|
| Injection Volume | 1.0 μl |
| Injection Mode | Direct injection |
| Injector Liner | Cyclo-Uniliner Liner, Siltek Deactivated, 4 × 6.3 × 78.5 mm, Restek cat.# 20338-214.5 |
| Injector Temperature | 220° C. |
| Detector Temperature | 250° C. |
| Carrier Gas | Helium at 3.0 psi |
| Detector | Flame ionization detector |
| Detector Gas | Hydrogen/air mixture |
| Gradient program | Initial temperature: 140°, hold for 15 minutes, ramp at 20° C./min for 5 minutes, final temp 240° C., hold for 1 minute at 240° |

The results for memantine hydrochloride provide additional evidence of the suitability of the matrix tablet technology for drugs containing the primary amine group. For example, Prototype 9-3 is a standard HPMC matrix tablet that shows first-order release of memantine. This formulation does not contain naproxen sodium or DSS. Prototype 9-2 is a comparable formulation with the addition of DSS. Retardation of drug release is seen in this case with the preservation of the first-order profile. Prototype 9-1 is a prototype containing memantine hydrochloride, naproxen sodium and DSS. The desirable zero-order release profile is achieved by the combination of components in this formulation.

Example 10

Preparation of Sustained Release Hydrophilic Matrix Tablets Containing Ritodrine Hydrochloride, Docusate Sodium (DSS) and Naproxen Sodium (NAP) at Benchtop Scale Each hydrophilic matrix tablet lot was produced by dry-blending the active substance(s) and excipients together followed by direct compression. The ritodrine hydrochloride and naproxen sodium were added together with all excipients in a 100 cc glass jar. Blending was accomplished using a GlobePharma Miniblend Table-Top Blender (10 min. @ 28 rpm). Aliquots of the blend were massed out using an analytical balance and were compressed using a Manesty DC16 press. Each tablet aliquot was added to the die manually and compressed at a speed of 3 rpm. Prototype 10-1 was compressed using 0.3750 in. round, concave Natoli tooling (HOB #91380) while prototypes 10-2 and 10-3 were compressed using 0.3125 in. round, concave Natoli tooling (HOB #91300). The compression force was varied until a tablet breaking force of 14-16 kp was consistently achieved.

TABLE 29

Prototype formulation compositions (mg/tablet)

Formulation (mg/tablet)

| Lot No. | Ritodrine Hydrochloride | Methocel K4M | Avicel PH-302 | Naproxen Sodium | Granular Docusate Sodium | Total Tablet Mass (mg) |
|---|---|---|---|---|---|---|
| Prototype 10-1 | 15.0 | 120.1 | 45.0 | 219.8 | 17.1 | 417.0 |
| Prototype 10-2 | 15.0 | 120.1 | 45.0 | 0.0 | 17.1 | 197.2 |
| Prototype 10-3 | 15.0 | 120.1 | 45.0 | 0.0 | 0.0 | 180.1 |

Ritodrine hydrochloride is taken orally as a tocolytic agent. The drug contains a secondary amine group and absorbs light in the UV region. Matrix tablets containing ritodrine were manufactured and evaluated with the goal of determining the applicability of the present invention to drugs containing the secondary amine functional group. The analysis of dissolution samples is done using HPLC with UV detection. External chromatographic standards were used to quantify the amount of ritodrine released.

Dissolution testing of matrix tablets was performed using USP Apparatus 2. At each specified time point, approximately 8 ml of media was removed using a stainless steel cannula. Samples were filtered using porous (full-flow) filters (QLA, Inc., Bridgewater, N.J., part number FIL035-01). A chromatographic standard was prepared with the final concentration of Ritodrine at ≈0.02 mg/ml. The diluent for preparing the chromatographic standards was dissolution media/acetonitrile in a 90%/10% volume/volume ratio. For each dissolution sample 1.0 ml was quantitatively transferred into an HPLC vial. An amount of acetonitrile (110 μl) was added to each HPLC vial to ensure a constant solvent composition between samples and standards. Every six samples were bracketed by chromatographic standards. Calculations were done by comparing the sample ritodrine peak area to the mean ritodrine peak area of the chromatographic standards. Drug released at each time point includes corrections for changes in vessel volume and the amount of drug removed during previous sample pulls. Dissolution media replacement was not performed. The system parameters for both the chromatographic and dissolution analysis are shown below.

TABLE 30

Dissolution parameters

| Parameters | Requirements |
|---|---|
| Method Type | USP Apparatus 2 (Paddle Method) |
| Rotation Speed | 50 rpm |
| Dissolution Media | pH 7.5 phosphate buffer (0.05M, potassium phosphate monobasic 0.68%/NaOH 0.164%) |
| Media Volume | 900 mL |
| Media Temperature | 37.0 ± 0.5 C. |
| Sampling Time Points | 1, 3, 6, 9, 12, 18 and 24 hours |
| Sampling Volume | 8 mL without media replacement (Use 35 μm Full-Flow Filter) |

TABLE 31

| HPLC Parameters | |
| --- | --- |
| System: | Agilent 1100 series HPLC system |
| Column: | Hypersil Gold (Thermo Scientific) C18, 250 × 4.6 mm ID, 5μ, 175 Å (Part No.: 25005-254630) |
| Detector: | UV detector, 270 nm |
| Mobile Phase A: | 75/25 (% v/% v) buffer/acetonitrile Buffer: 0.02M $KH_2PO_4$ (adjust to final pH of 4.0 with $H_3PO_4$) |
| Method Type: | Isocratic |
| Flow Rate: | 1.0 mL/min |
| Injection Volume: | 15 μL |
| Run Time: | 10.00 minutes |
| Peakwidth: | >0.1 min |
| Column Temperature: | 35° C. |
| Autosampler temp: | Ambient |

The results show the validity of the matrix tablet technology for drugs containing the secondary amine functional group. Prototype 10-3 shows the first-order release that is typical for hydrophilic matrix tablet systems. Consistent with the other Examples, the addition of docusate retards release (Prototype 10-2). Prototype 10-1 contains a combination of components (ritodrine, naproxen sodium, and docusate) that permits zero-order release to be obtained.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

What is claimed is:

1. A sustained-release oral pharmaceutical composition comprising within a single dosage form:
   a hydrophilic matrix comprising a cellulose ether selected from the group consisting of a hydroxyalkyl cellulose, a carboxyalkyl cellulose, and a combination thereof;
   a therapeutically effective amount of a non-opioid amine-containing compound; and
   a salt of a non-steroidal anti-inflammatory drug (NSAID);
   wherein the non-opioid amine-containing compound and the salt of an NSAID are within the hydrophilic matrix; and
   wherein the composition exhibits a release profile with respect to the non-opioid amine-containing compound, wherein the release profile comprises a substantial portion that is representative of zero-order release kinetics under in vitro conditions as a result of dissolution of the hydrophilic matrix.

2. The composition of claim 1, wherein cellulose ether comprises hydroxypropyl methylcellulose.

3. The composition of claim 1, further comprising microcrystalline cellulose.

4. The composition of claim 1, wherein the non-opioid amine-containing compound comprises a tertiary amine.

5. The composition of claim 1, wherein the non-opioid amine-containing compound is selected from the group consisting of dextromethorphan, cyclobenzaprine, benztropine, baclofen, arbaclofen, ritodrine, tizanidine, flurazepam, chlorpheniramine, doxylamine, diphenhydramine, diltiazem, rimantadine, amantadine, memantine, and combinations thereof.

6. The composition of claim 1, wherein the non-opioid amine-containing compound is a salt comprising a hydrochloride, a bitartrate, an acetate, a naphthylate, a tosylate, a mesylate, a besylate, a succinate, a palmitate, a stearate, an oleate, a pamoate, a laurate, a valerate, a hydrobromide, a sulfate, a methane sulfonate, a tartrate, a citrate, a maleate, or a combination of the foregoing.

7. The composition of claim 1, wherein the NSAID salt is selected from the group consisting of a salicylate derivative, a 2-aryl propionic acid derivative, a pyrazolidine derivative, an N-arylanthranilic acid derivative, an oxicam derivative, an arylalkanoic acid, an indole derivative, and combinations thereof.

8. The composition of claim 1, wherein the NSAID salt is present in an amount effective to provide zero-order release kinetics of the non-opioid amine-containing compound from the hydrophilic matrix under in vitro conditions.

9. The composition of claim 1, further comprising a pharmaceutically acceptable anionic surfactant, wherein the non-opioid amine-containing compound, the salt of an NSAID, and the anionic surfactant are within the hydrophilic matrix.

10. The composition of claim 9, wherein the pharmaceutically acceptable anionic surfactant is selected from the group consisting of monovalent alkyl carboxylates, acyl lactylates, alkyl ether carboxylates, N-acyl sarcosinates, polyvalent alkyl carbonates, N-acyl glutamates, fatty acid-polypeptide condensates, sulfur-containing surfactants, phosphated ethoxylated alcohols, and combinations thereof.

11. The composition of claim 9, wherein the pharmaceutically acceptable anionic surfactant is present in an amount effective to modify the rate of release of the non-opioid amine-containing compound from the hydrophilic matrix.

12. The composition of claim 1, wherein the single dosage form is a tablet form.

13. A sustained-release oral pharmaceutical composition comprising within a single dosage form:
   a hydrophilic matrix comprising a cellulose ether;
   a therapeutically effective amount of an amine-containing compound selected from the group consisting of dextromethorphan, cyclobenzaprine, benztropine, ritodrine, memantine, amantadine, salts thereof, and combinations thereof; and
   a salt of a non-steroidal anti-inflammatory drug (NSAID) selected from the group consisting of a salt of naproxen, diclofenac, ibuprofen, and combinations thereof;
   wherein the amine-containing compound and the salt of an NSAID are within the hydrophilic matrix; and
   wherein the composition exhibits a release profile of the amine-containing compound, wherein the release profile comprises a substantial portion that is representative of zero-order release kinetics under in vitro conditions.

14. The composition of claim 13, wherein the cellulose ether comprises a hydroxyalkyl cellulose, a carboxyalkyl cellulose, or a combination thereof.

15. The composition of claim 13, wherein cellulose ether comprises hydroxypropyl methylcellulose.

16. The composition of claim 13, further comprising microcrystalline cellulose.

17. A sustained-release oral pharmaceutical composition comprising within a single dosage form:

a hydrophilic matrix comprising a cellulose ether selected from the group consisting of a hydroxyalkyl cellulose, a carboxyalkyl cellulose, and a combination thereof;

a therapeutically effective amount of an amine-containing compound selected from the group consisting of dextromethorphan, cyclobenzaprine, benztropine, ritodrine, memantine, amantadine, salts thereof, and combinations thereof;

a salt of a non-steroidal anti-inflammatory drug (NSAID) selected from the group consisting of a salt of naproxen, diclofenac, ibuprofen, and combinations thereof; and a pharmaceutically acceptable anionic surfactant selected from the group consisting of sodium lauryl sulfate, docusate sodium, docusate calcium, and combinations thereof;

wherein the amine-containing compound, the salt of an NSAID, and the anionic surfactant are within the hydrophilic matrix; and wherein the composition exhibits a release profile of the amine-containing compound, wherein the release profile comprises a substantial portion that is representative of zero-order release kinetics under in vitro conditions.

18. The composition of claim 17, wherein cellulose ether comprises hydroxypropyl methylcellulose.

19. The composition of claim 17, further comprising microcrystalline cellulose.

* * * * *